US012629413B2

(12) United States Patent
Zloza et al.

(10) Patent No.: US 12,629,413 B2
(45) Date of Patent: May 19, 2026

(54) UTILIZING VACCINES TO TREAT CANCER AND ENHANCE THE SUCCESS RATE OF CANCER IMMUNOTHERAPY

(71) Applicant: Rush University Medical Center, Chicago, IL (US)

(72) Inventors: Andrew Zloza, Hinsdale, IL (US); Jenna H. Newman, Boston, MA (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 693 days.

(21) Appl. No.: 17/134,663

(22) Filed: Dec. 28, 2020

(65) Prior Publication Data

US 2021/0196813 A1 Jul. 1, 2021

Related U.S. Application Data

(60) Provisional application No. 62/954,154, filed on Dec. 27, 2019.

(51) Int. Cl.
*A61K 39/145* (2006.01)
*A61K 45/06* (2006.01)
*A61P 35/00* (2006.01)
*A61K 39/00* (2006.01)

(52) U.S. Cl.
CPC ............ *A61K 39/145* (2013.01); *A61K 45/06* (2013.01); *A61P 35/00* (2018.01); *A61K 2039/5252* (2013.01); *A61K 2039/54* (2013.01); *A61K 2039/545* (2013.01); *A61K 2039/585* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 4,880,078 A | 11/1989 | Inoue et al. | |
| 5,290,540 A | 3/1994 | Prince et al. | |
| 5,374,548 A | 12/1994 | Caras | |
| 5,399,331 A | 3/1995 | Loughrey et al. | |
| 5,416,016 A | 5/1995 | Low et al. | |
| 5,855,913 A | 1/1999 | Hanes et al. | |
| 5,874,064 A | 2/1999 | Edwards et al. | |
| 5,934,272 A | 8/1999 | Lloyd et al. | |
| 5,985,309 A | 11/1999 | Edwards et al. | |
| 5,985,320 A | 11/1999 | Edwards et al. | |
| 6,019,968 A | 2/2000 | Platz et al. | |
| 6,316,024 B1 | 11/2001 | Allen et al. | |
| 6,350,466 B1 | 2/2002 | Li et al. | |
| 10,639,366 B2 * | 5/2020 | Deng ................. | A61P 35/00 |
| 2002/0086284 A1 * | 7/2002 | Coffey ................ | A61K 35/765 |
| | | | 435/5 |
| 2022/0339223 A1 * | 10/2022 | Gromeier ............. | A61P 1/00 |

FOREIGN PATENT DOCUMENTS

| | | |
|---|---|---|
| WO | 9219244 A2 | 11/1992 |
| WO | 9732572 A2 | 9/1997 |
| WO | 9744013 A1 | 11/1997 |
| WO | 9831346 A1 | 7/1998 |
| WO | 9966903 A2 | 12/1999 |

OTHER PUBLICATIONS

Rosato et al., Nature Communications | (2019) 10:567 (Year: 2019).*
Hamilton et al., Cell Reports, vol. 22, Issue 1, Jan. 2, 2018, pp. 1-7 (Year: 2018).*
Burke Cytokine and Growth Factors Review vol. 21, pp. 99-102). (Year: 2010).*
Monod et al., IMGT/JunctionAnalysis: the first tool for the analysis of the immunoglobulin and T cell receptor complex V-J and V-D-J Junctions. Bioinformatics 20 Suppl 1, 1379-385 (2004).
Simoni et al., Bystander CD8(+) T cells are abundant and phenotypically distinct in human tumour infiltrates. Nature 657, 575-579 (2018).
Martínez-Lostao et al., How Do Cytotoxic Lymphocytes Kill Cancer Cells? Clinical Cancer Research 21, 5047-5056 (2015).
Mauri, M. Menon, Human regulatory B cells in health and disease: therapeutic potential. The Journal of clinical investigation 127, 772-779 (2017).
Milgrom et al, (1999) New Engl. J. Med. 341 : 1966-1973.
Monod et al., IMGT/JunctionAnalysis: the first tool for the analysis of the immunoglobulin and T cell receptor complex V-J and V-D-J Junctions. Bioinformatics 20 Suppl 1, i379-385 (2004).
Newman et al., Infection: a Cause of and Cure for Cancer. Current pharmacology reports 3, 315-320 (2017).
O'Hagan, et al., The mechanism of action of MF59—an innately attractive adjuvant formulation. Vaccine 30, 4341-4348 (2012).
Old et al., Effect of Bacillus Calmette-Guerin infection on transplanted tumours in the mouse. Nature 184(Suppl 5), 291-292 (1959).
Owais et al., (1995) Antimicrob. Agents Chemother. 39: 180.
Portieljie et al, (2003) Cancer Immunol. Immunother. 52: 133-144.
Ranade, (1989) J. Clin. Pharmacol. 29:685.
Robins et al., Comprehensive assessment of T-cell receptor beta-chain diversity in alphabeta T cells. Blood 114, 4099-4107 (2009).
Rosato et al., Virus-specific memory T cells populate tumors and can be repurposed for tumor immunotherapy. Nature communications 10, 567 (2019).
Rosenberg et al., Antitumor effects in mice of the intravenous injection of attenuated *Salmonella typhimurium.* Journal of immunotherapy 25, 218-225 (2002).
Rosser et al., Regulatory B cells: origin, phenotype, and function. Immunity 42, 607-612 (2015).
Rutigliano et al., Highly pathological influenza A virus infection is associated with augmented expression of PD-1 by functionally compromised virus-specific CD8+ T cells. Journal of virology 88, 1636-1651 (2014).

(Continued)

*Primary Examiner* — Shanon A. Foley
*Assistant Examiner* — Myron G Hill
(74) *Attorney, Agent, or Firm* — Barnes & Thornburg, LLP

(57) ABSTRACT

Methods treating cancer are provided. The methods include intratumorally administering a therapeutically effective dose of a vaccine to a subject in need thereof.

19 Claims, 18 Drawing Sheets

Specification includes a Sequence Listing.

(56) References Cited

OTHER PUBLICATIONS

Sasaki et al., Modeling for influenza vaccines and adjuvants profile for safety prediction system using gene expression profiling and statistical tools. PloS one 13, e0191896 (2018).

Schreibelt et al., Commonly used prophylactic vaccines as an alternative for synthetically produced TLR ligands to mature monocyte-derived dendritic cells. Blood 116, 564-574 (2010).

Schreier et al, (1994) J. Biol. Chem. 269:9090.

Serradell et al., Efficient oral vaccination by bioengineering virus-like particles with protozoan surface proteins. Nature communications 10, 361 (2019).

Sharpe, Introduction to checkpoint inhibitors and cancer immunotherapy. Immunological reviews 276, 5-8 (2017).

Shayan et al., Phase Ib Study of Immune Biomarker Modulation with Neoadjuvant Cetuximab and TLR8 Stimulation in Head and Neck Cancer to Overcome Suppressive Myeloid Signals. Clinical cancer research : an official journal of the American Association for Cancer Research 24, 62-72 (2018).

Shultz et al., Human lymphoid and myeloid cell development in NOD/LtSz-scid IL2R gamma null mice engrafted with mobilized human hemopoietic stem cells. Journal of immunology 174, 6477-6489 (2005).

Sidman et al., (1983) Biopolymers 22:547-556.

Simoni et al., Bystander CD8(+) T cells are abundant and phenotypically distinct in human tumour infiltrates. Nature 557, 575-579 (2018).

Slamon et al, (2001) New Engl. J. Med. 344:783-792.

Smed-Sorensen et al., Influenza A virus infection of human primary dendritic cells impairs their ability to cross-present antigen to CD8 T cells. PLoS pathogens 8, e1002572 (2012).

Snyder et al., Genetic basis for clinical response to CTLA-4 blockade in melanoma. The New England journal of medicine 371, 2189-2199 (2014).

Tegenge et al., Pharmacokinetics and biodistribution of squalene-containing emulsion adjuvant following intramuscular injection of H5N1 influenza vaccine in mice. Regulatory toxicology and pharmacology : RTP 81, 113-119 (2016).

Thompson et al., Tumor masses support naive T cell infiltration, activation, and differentiation into effectors. J Exp Med 207, 1791-1804 (2010).

Topalian et al., Five-Year Survival and Correlates Among Patients With Advanced Melanoma, Renal Cell Carcinoma, or Non-Small Cell Lung Cancer Treated With Nivolumab. JAMA oncology 10.1001/jamaoncol.2019.2187 (2019).

Tsai, Fluad(R)-MF59(R)-Adjuvanted Influenza Vaccine in Older Adults. Infection & chemotherapy 45, 159-174 (2013).

Tumeh et al., PD-1 blockade induces responses by inhibiting adaptive immune resistance. Nature 515, 568-571 (2014).

Umezawa et al, (1988) Biochem. Biophys. Res. Commun. 153: 1038.

Wilkinson et al., Further Advances in Cancer Immunotherapy: Going Beyond Checkpoint Blockade. Frontiers in immunology 9, 1082-1082 (2018).

Wu et al., High-throughput sequencing detects minimal residual disease in acute T lymphoblastic leukemia. Science translational medicine 4, 134ra163 (2012).

Xin et al., Pathogen boosted adoptive cell transfer immunotherapy to treat solid tumors. Proceedings of the National Academy of Sciences 114, 740-745 (2017).

Yang et al, (2003) New Engl. J. Med. 349:427-434.

Young-Xu et al., The Annual Burden of Seasonal Influenza in the US Veterans Affairs Population. PloS one 12, e0169344-e0169344 (2017).

Yuen et al., B lymphocytes and cancer: a love-hate relationship. Trends in cancer 2, 747-757 (2016).

Zloza et al., NKG2D signaling on CD8(+) T cells represses T-bet and rescues CD4-unhelped CD8(+) T cell memory recall but not effector responses. Nature medicine 18, 422-428 (2012).

Zloza, Viruses, bacteria, and parasites—oh my! a resurgence of interest in microbial-based therapy for cancer. Journal for immunotherapy of cancer 6, 3 (2018).

Alsaab et al., PD-1 and PD-L1 Checkpoint Signaling Inhibition for Cancer Immunotherapy: Mechanism, Combinations, and Clinical Outcome. Frontiers in pharmacology 8, 561-561 (2017).

Andersen et al., Dissection of T-cell antigen specificity in human melanoma. Cancer research 72, 1642-1650 (2012).

Ayers et al., IFN-gamma-related mRNA profile predicts clinical response to PD-1 blockade. The Journal of clinical investigation 127, 2930-2940 (2017).

Baert et al., (2003) New Engl. J. Med. 348:601-608.

Beniaminovitz et al, (2000) New Engl. J. Med. 342:613-619.

Binnewies et al., Understanding the tumor immune microenvironment (TIME) for effective therapy. Nature medicine 24, 541-550 (2018).

Bloemen et al, (1995) FEBS Lett. 357: 140.

Brincker, 1993. Crit. Rev. Oncol. Hematol. 15(2):91-8.

Briscoe et al, (1995) Am. J. Physiol. vol. 268, Issue 3, L374-L380.

Bu et al., Learning from PD-1 Resistance: New Combination Strategies. Trends in molecular medicine 22, 448-451 (2016).

Cann et al., Acute infections as a means of cancer prevention: opposing effects to chronic infections? Cancer detection and prevention 30, 83-93 (2006).

Carlson et al., Using synthetic templates to design an unbiased multiplex PCR assay. Nature communications 4, 2680 (2013).

CDC (2018) https://www.cdc.gov/flu/fluvaxview/coverage-1718estimates.htm.

Celikoglu et al., 2008. Cancer Therapy 6, 545-552.

Mapara et al., Tolerance and Cancer: Mechanisms of Tumor Evasion and Strategies for Breaking Tolerance. Journal of Clinical Oncology 22, 1136-1151 (2004).

Coley, The Treatment of Inoperable Sarcoma by Bacterial Toxins (the Mixed Toxins of the *Streptococcus erysipelas* and the Bacillus prodigiosus). Proceedings of the Royal Society of Medicine 3, 1-48 (1910).

Cristescu et al., Pan-tumor genomic biomarkers for PD-1 checkpoint blockade-based immunotherapy. Science 362 (2018).

Dai et al., Intratumoral delivery of inactivated modified vaccinia virus Ankara (iMVA) induces systemic antitumor immunity via STING and Batf3-dependent dendritic cells. Science immunology 2 (2017).

Dang et al., Combination bacteriolytic therapy for the treatment of experimental tumors. Proceedings of the National Academy of Sciences 98, 15155-15160 (2001).

Emerson et al., High-throughput sequencing of T-cell receptors reveals a homogeneous repertoire of tumour-infiltrating lymphocytes in ovarian cancer. The Journal of pathology 231, 433-440 (2013).

Epstein et al, (1985) Proc. Natl. Acad. Sci. USA 82:3688-3692.

Erkes et al., Virus-Specific CD8(+) T Cells Infiltrate Melanoma Lesions and Retain Function Independently of PD-1 Expression. Journal of immunology 198, 2979-2988 (2017).

Forbes et al., White paper on microbial anti-cancer therapy and prevention. Journal for immunotherapy of cancer 6, 78 (2018).

Gajewski et al., Cancer Immunotherapy Targets Based on Understanding the T Cell-Inflamed Versus Non-T Cell-Inflamed Tumor Microenvironment. Advances in experimental medicine and biology 1036, 19-31 (2017).

Galon et al., Approaches to treat immune hot, altered and cold tumours with combination immunotherapies. Nature reviews. Drug discovery 10.1038/s41573-018-0007-y (2019).

Ghosh et al, (2003) New Engl. J. Med. 348:24-32.

Goff et al., Adjuvants and immunization strategies to induce influenza virus hemagglutinin stalk antibodies. PloS one 8, e79194 (2013).

Hammerich et al., Systemic clinical tumor regressions and potentiation of PD1 blockade with in situ vaccination. Nature medicine 25, 814-824 (2019).

Herold et al, (2002) New Engl. J. Med. 346: 1692-1698.

Hildner et al., Batf3 deficiency reveals a critical role for CD8alpha+ dendritic cells in cytotoxic T cell immunity. Science 322, 1097-1100 (2008).

Hwang et al., (1980) Proc. Natl. Acad. Sci. USA 77:4030-4034.

(56) References Cited

OTHER PUBLICATIONS

Iheagwara et al., Influenza virus infection elicits protective antibodies and T cells specific for host cell antigens also expressed as tumor-associated antigens: a new view of cancer immunosurveillance. Cancer immunology research 2, 263-273 (2014).

Jenkins et al., Addition of a prominent epitope affects influenza A virus-specific CD8+ T cell immunodominance hierarchies when antigen is limiting. Journal of immunology 177, 2917-2925 (2006).

Kather et al., Topography of cancer-associated immune cells in human solid tumors. eLife 7 (2018).

Kaufman et al., Oncolytic viruses: a new class of immunotherapy drugs. Nature reviews. Drug discovery 14, 642-662 (2015).

Keinanen, Laukkanen (1994) FEBS Lett. 346: 123.

Khurana et al., MF59 adjuvant enhances diversity and affinity of antibody-mediated immune response to pandemic influenza vaccines. Science translational medicine 3, 85ra48 (2011).

Killion et al., (1994) Immunomethods 4:273.

Knudsen et al., Different human vaccine adjuvants promote distinct antigen-independent immunological signatures tailored to different pathogens. Scientific reports 6, 19570 (2016).

Kohler et al., Enhanced tumor susceptibility of immunocompetent mice infected with lymphocytic choriomeningitis virus. Cancer immunology, immunotherapy : CII 32, 117-124 (1990).

Kohlhapp et al., Non-oncogenic Acute Viral Infections Disrupt Anti-cancer Responses and Lead to Accelerated Cancer-Specific Host Death. Cell reports 17, 957-965 (2016).

Kumlin et al., Sialic acid tissue distribution and influenza virus tropism. Influenza and other respiratory viruses 2, 147-154 (2008).

Kvistborg et al., TIL therapy broadens the tumor-reactive CD8(+) T cell compartment in melanoma patients. Oncoimmunology 1, 409-418 (2012).

Langer (1982) Chem. Tech. 12:98-105.

Langer et al., (1981) J. Biomed. Mater. Res. 15: 167-277.

Lindau et al., The immunosuppressive tumour network: myeloid-derived suppressor cells, regulatory T cells and natural killer T cells. Immunology 138, 105-115 (2013).

Lipsky et al, (2000) New Engl. J. Med. 343: 1594-1602.

Liu et al, (1999) J. Neurol. Neurosurg. Psych. 67:451-456.

Makkouk, G. J. Weiner, Cancer immunotherapy and breaking immune tolerance: new approaches to an old challenge. Cancer research 75, 5-10 (2015).

* cited by examiner

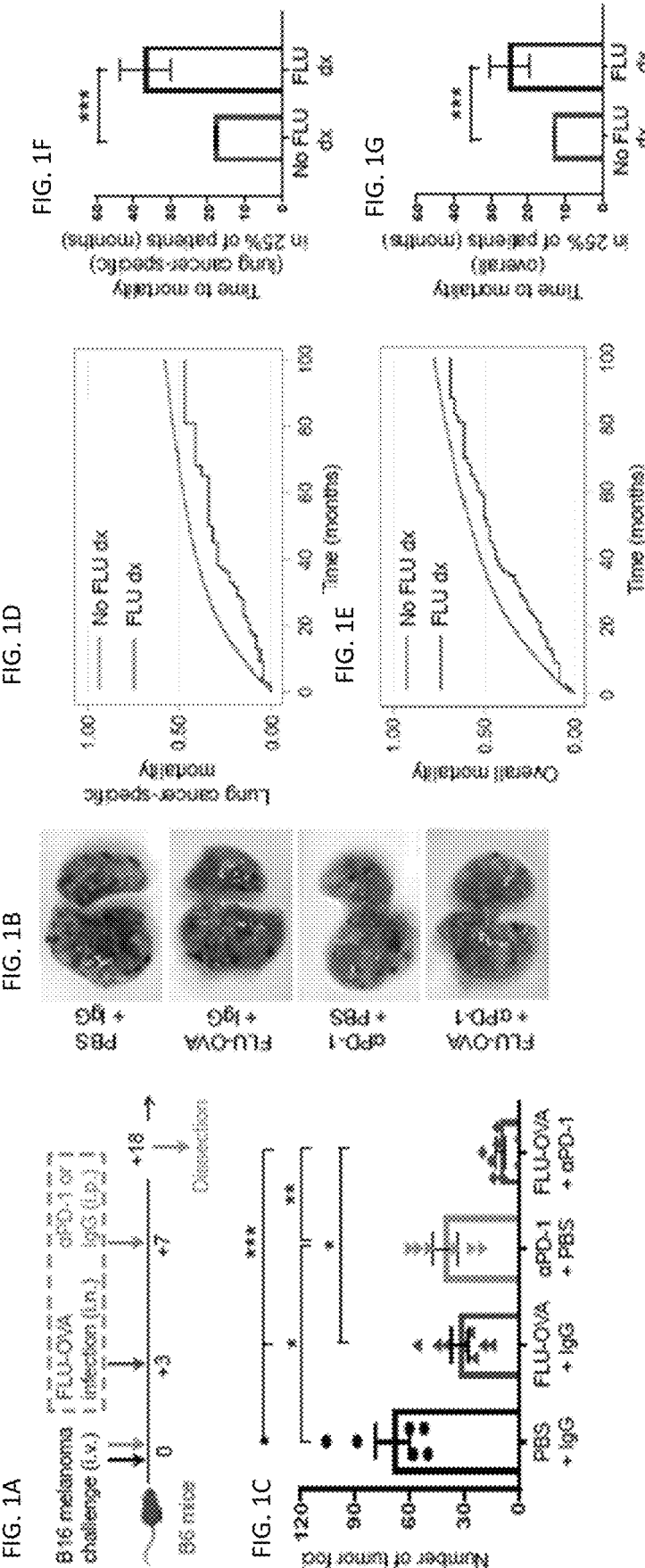

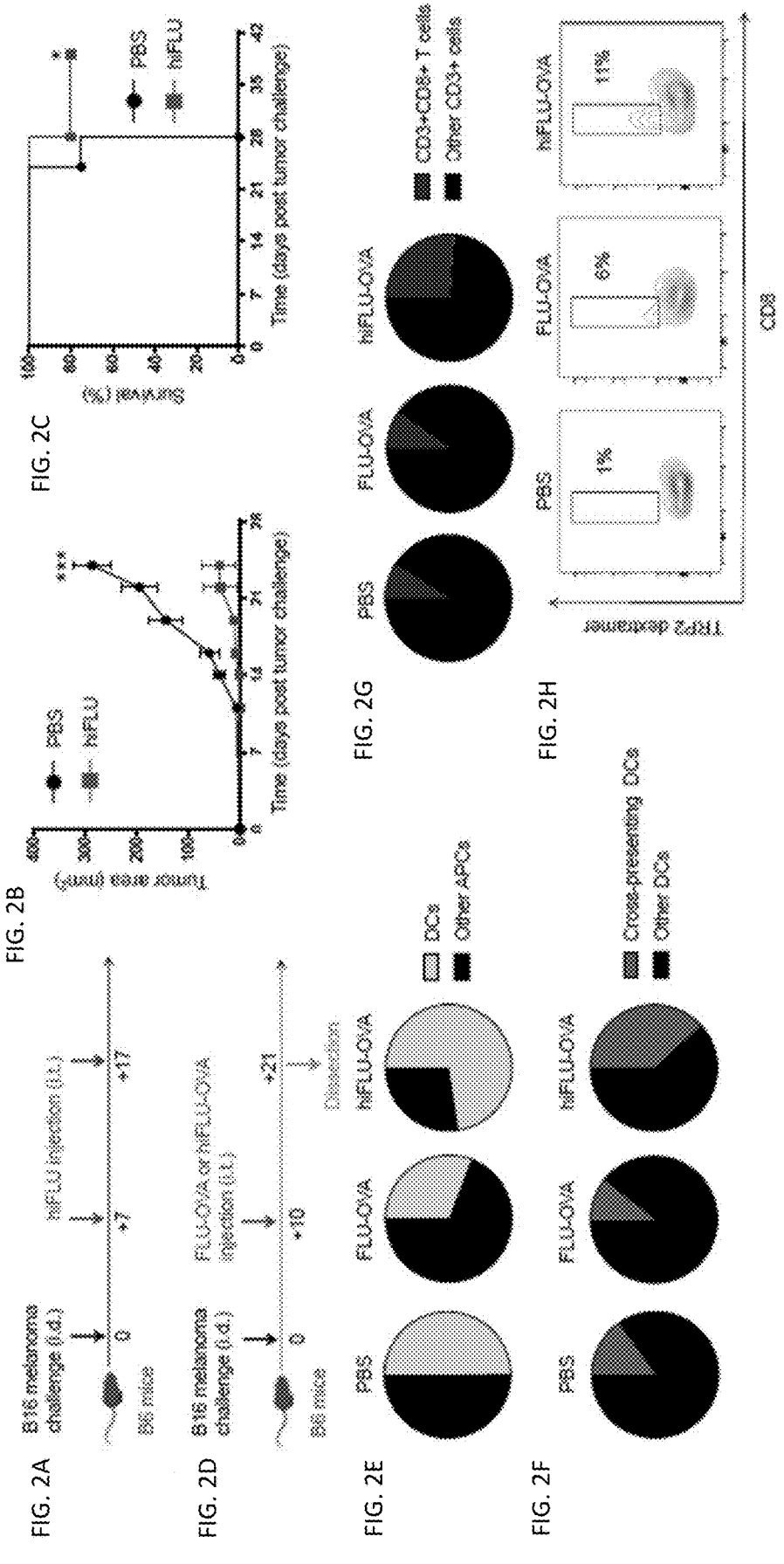

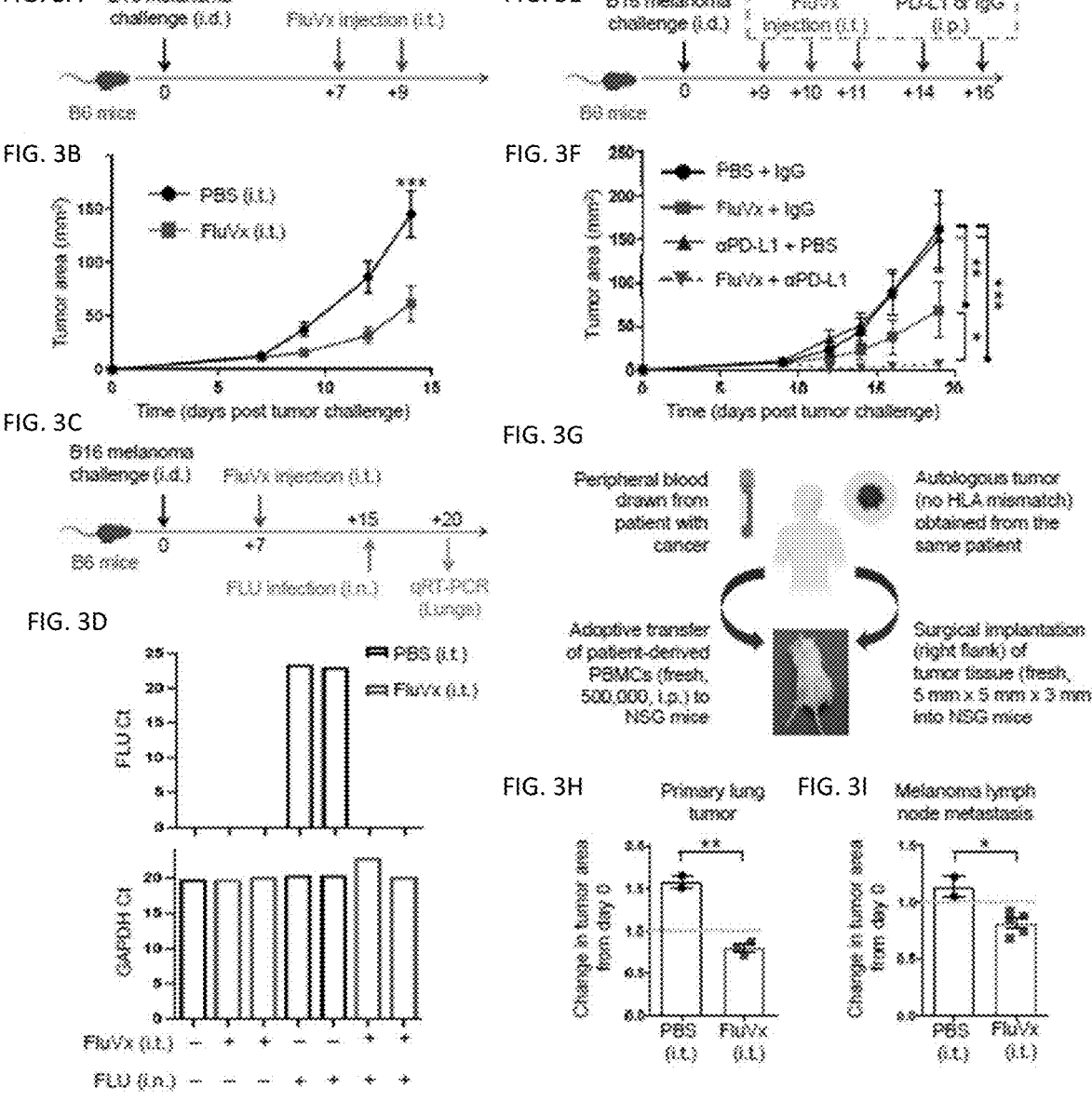

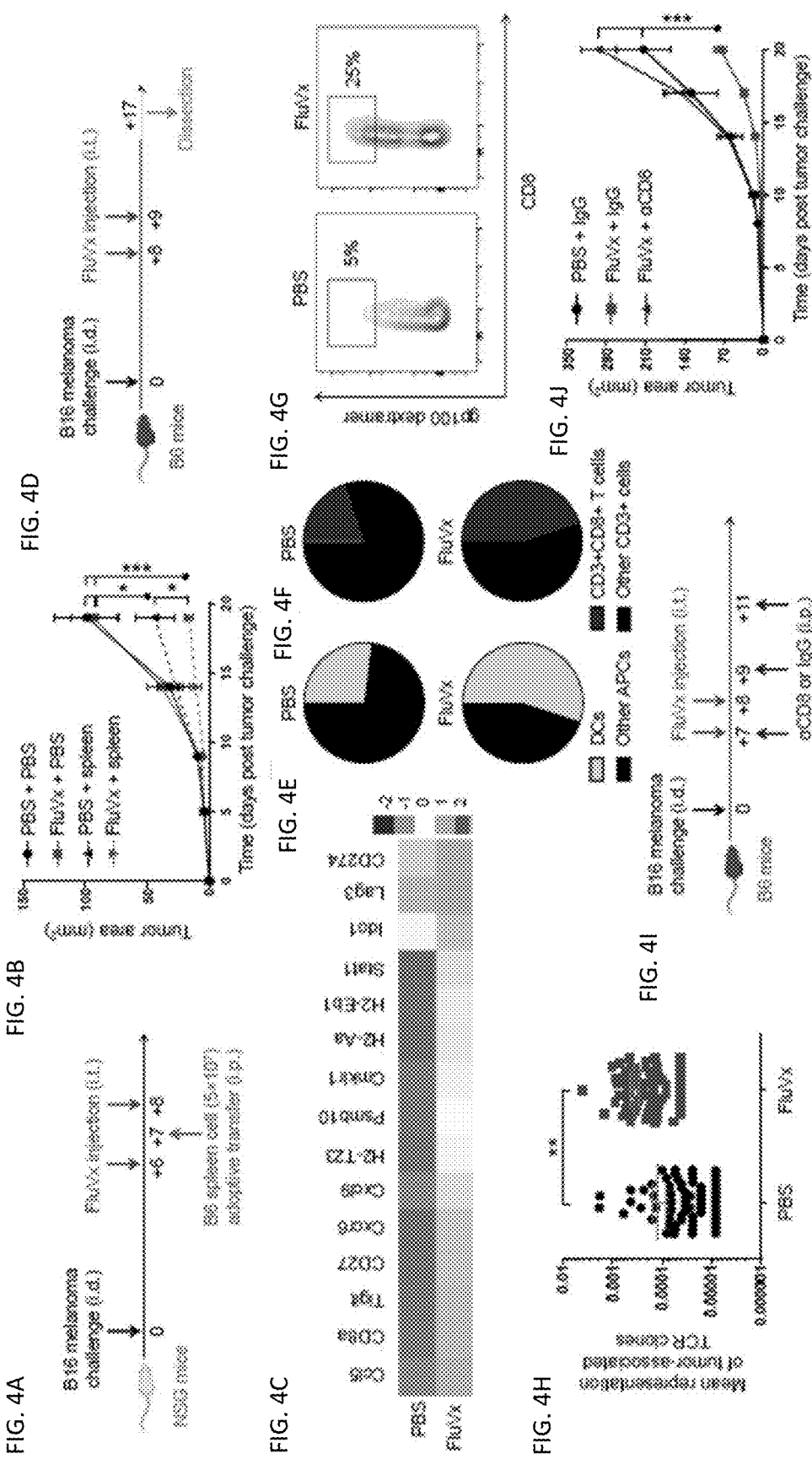

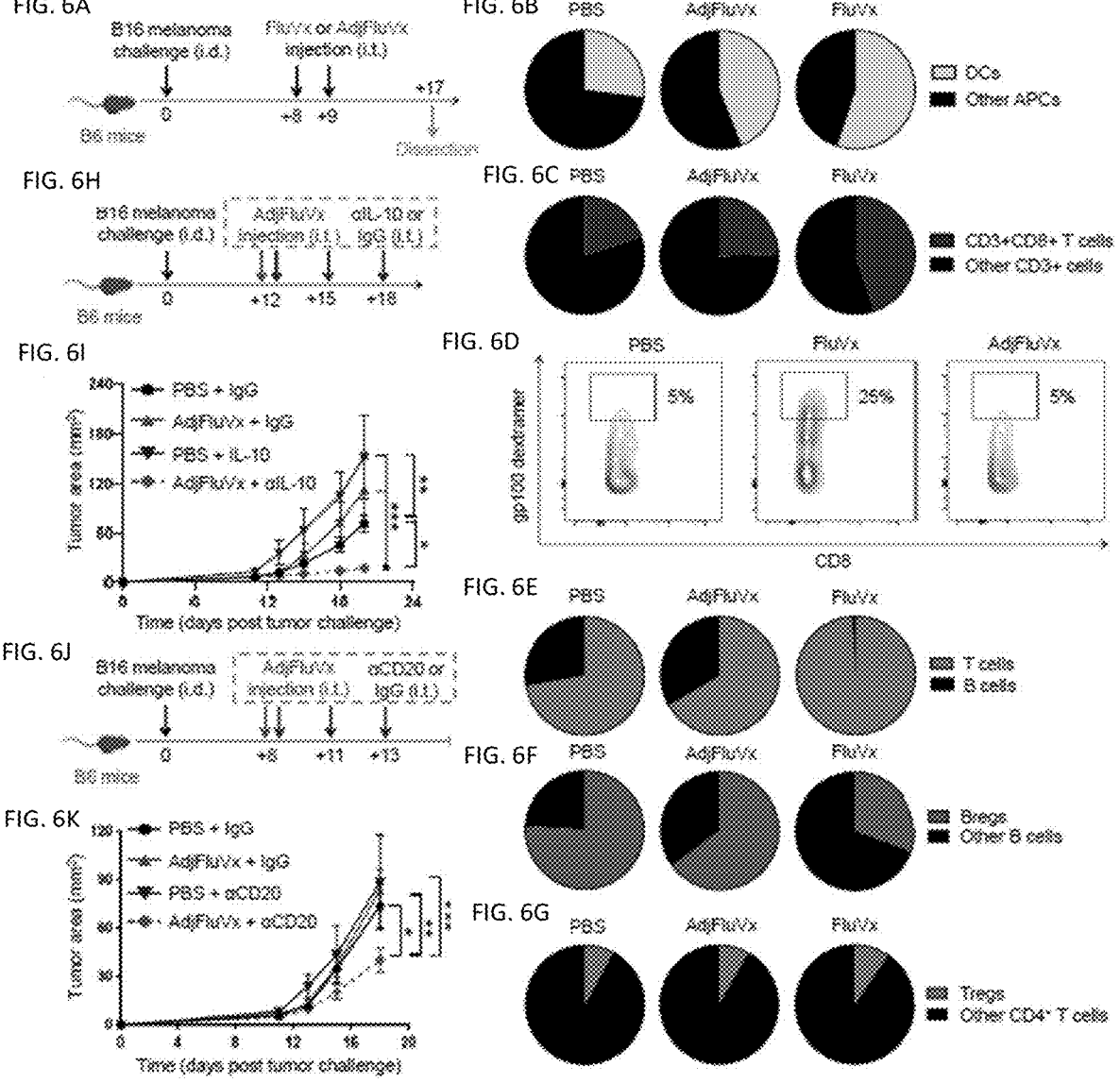

FIG. 7A        FIG. 7B        FIG. 7C
FIG. 7D        FIG. 7E        FIG. 7F
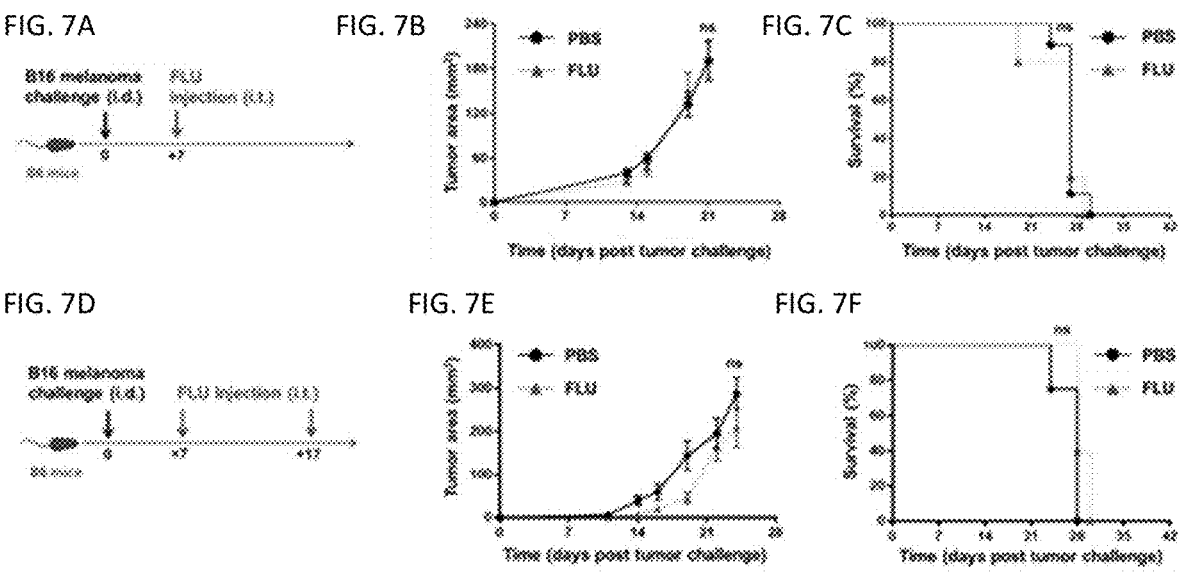
FIG. 8A
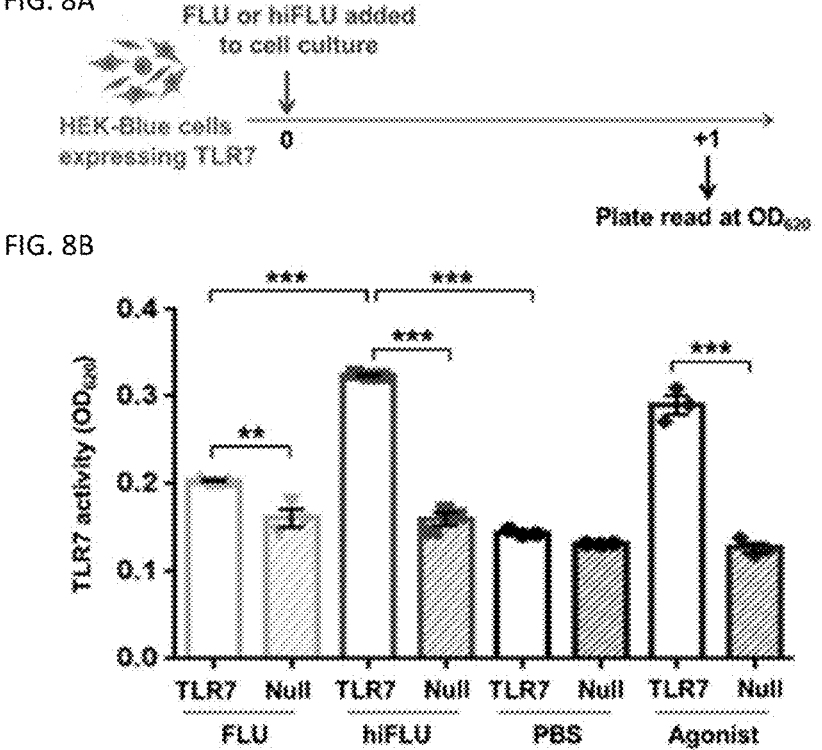
FIG. 8B FIG. 11A
FIG. 11C
FIG. 11B
FIG. 11D
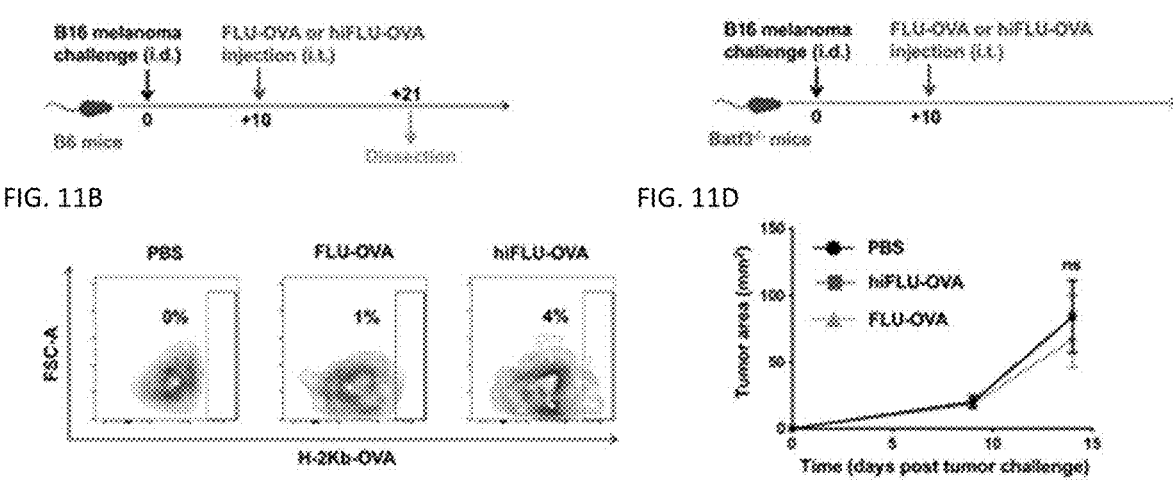
FIG. 12A
FIG. 12B
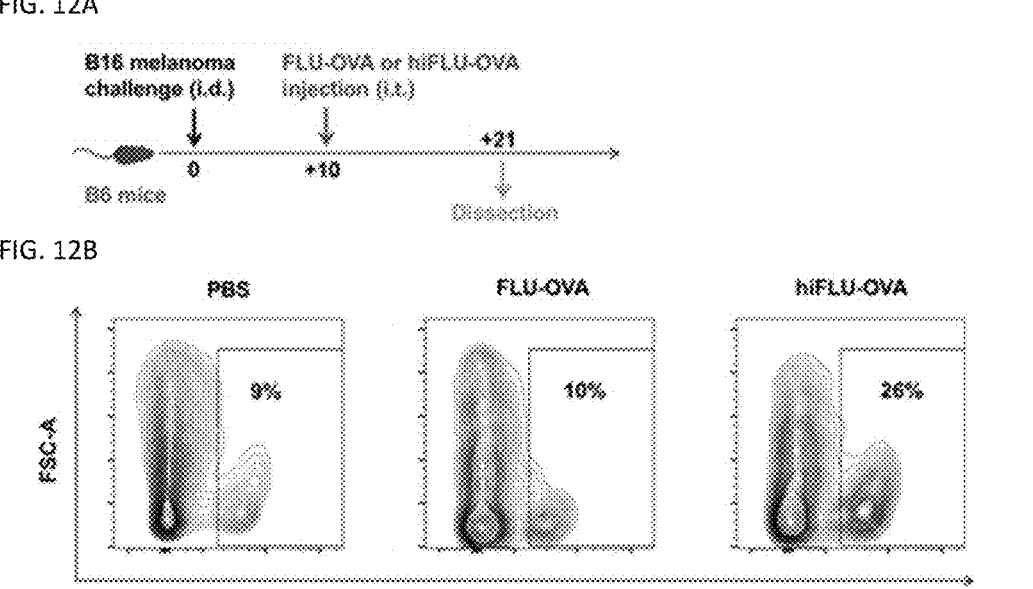

FIG. 17A
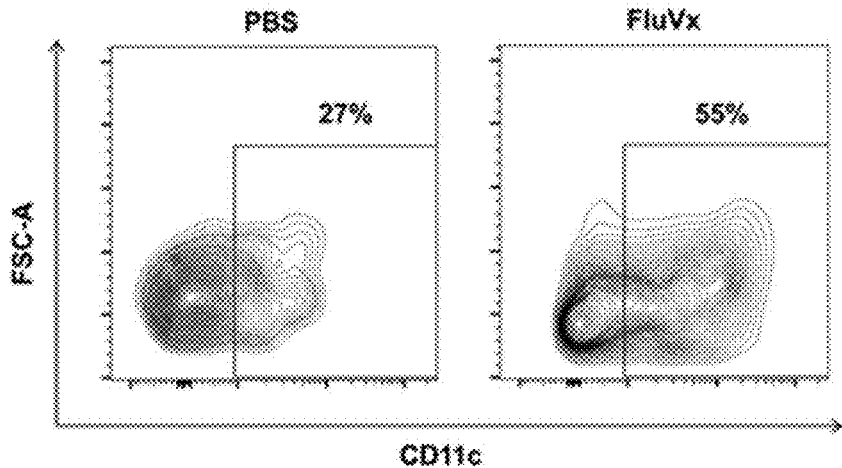
FIG. 17B
FIG. 17C
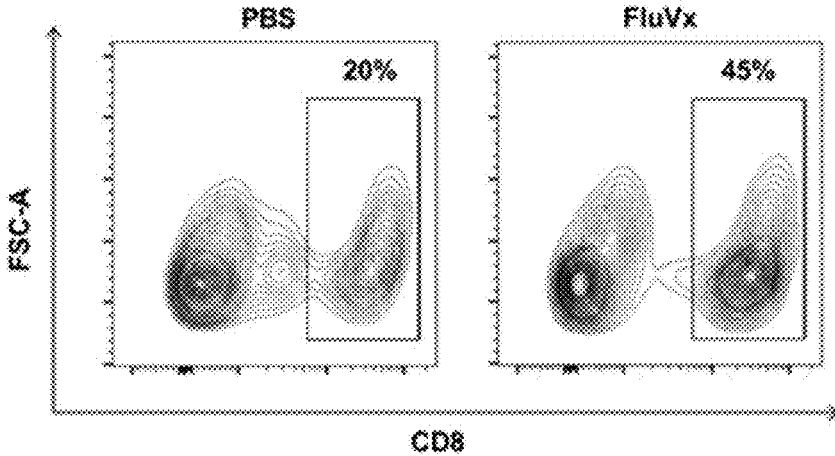

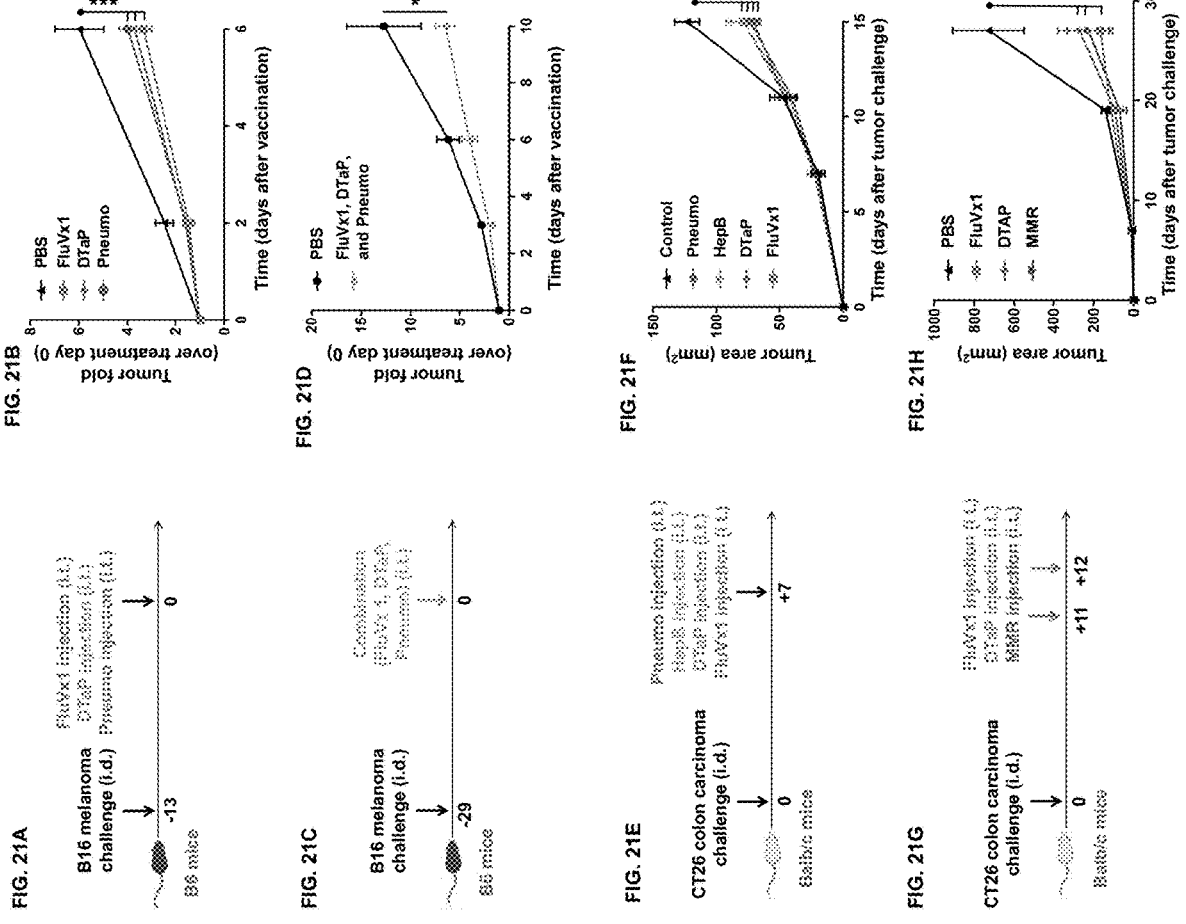

UTILIZING VACCINES TO TREAT CANCER AND ENHANCE THE SUCCESS RATE OF CANCER IMMUNOTHERAPY

RELATED APPLICATIONS

This application claims the benefit of the filing date of U.S. Provisional Patent Application No. 62/954,154, filed Dec. 27, 2019, the contents of which is hereby incorporated by reference.

SEQUENCE LISTING

The instant application contains a Sequence Listing which has been submitted electronically in ASCII format and is hereby incorporated by reference in its entirety. The ASCII copy, created on Dec. 21, 2020, is named 42960-322480 Sequence Listing_ST25.txt and is 2 KB in size.

BACKGROUND

1. Technical Field Text

The present disclosure relates to methods for treating cancer and to methods for enhancing the success rate of cancer immunotherapy, and in particular the methods utilizing vaccines for treating cancer and for enhancing the success rate of cancer immunotherapy.

2. Background Information

The tumor microenvironment represents a significant barrier that restricts immune responses against tumors and limits the efficacy of currently available immunotherapies as treatments for cancer. However, immune infiltration of tumors, especially by $CD8^+$ T cells, has been shown to correlate with augmented responses to immunotherapy and improved survival (1-5). An immunologically inflamed ("hot") tumor microenvironment exhibits robust antigen presentation and T cell activation, contributing to the development of tumor-specific $CD8^+$ T cell functionality that can acutely eliminate cancer cells, generate systemic tumor-specific immunity, and form long-term anti-tumor memory responses (5, 6). However, a significant proportion of patients harbor a immunologically "cold" tumor microenvironment that is either devoid of immune cell infiltration (an "immune desert") or that is predominantly infiltrated by suppressive regulatory cell subtypes (including regulatory T cells [Tregs], regulatory B cells [Bregs], and myeloid-derived suppressor cells [MDSCs]) (7-9). In both environments, cancer growth is immunologically unchecked and recruitment of inflammatory immune cells into such tumors is imperative for anti-tumor responses. Recently, cancer immunotherapy, including blockade of inhibitory immune checkpoints (such as PD-1/PD-L1 and CTLA-4), has emerged as an unprecedented breakthrough for the treatment of cancer that can induce long-term tumor regression (10-12). However, responses to such therapies have been demonstrated to be effective only in select patients, particularly those who harbor a "hot" tumor microenvironment (13). Therefore, to increase response rates to immunotherapy, innovative solutions are needed to convert "cold" tumor microenvironments to "hot" by increasing infiltration of inflammatory immune cells that can serve as targets for immunotherapies in tumors devoid of immune infiltration and can overcome local immunosuppression in tumors infiltrated by regulatory cells.

One approach that could be utilized involves inducing a strong immune response, unrelated to the immune response against the cancer, within the tumor microenvironment that could then serve as a catalyst for a strong tumor-specific immune response. This concept employs a basic tenet of immunology, that responses against foreign antigens are strong and that responses against self-antigens are inherently weak. Towards avoiding autoimmunity, the immune system has developed many tolerance mechanisms by which strong responses to self-antigens are prevented or eliminated (14-16). Because tumors develop from initially normal cells, many of the antigens of the tumor are self-antigens or antigens similar to self-antigens, and mounting an effective immune response against such antigens is a challenge. This undertaking is made even more difficult by the immunosuppressive nature of the tumor, which increases the immune-activation threshold necessary to be reached before tolerance is broken and potent responses to tumor antigens are mounted. However, when recognizing foreign components (like those associated with pathogens), the immune system is capable of developing strong responses even within the tumor microenvironment (17), and thus, components of pathogens (which can engage receptors associated with innate immunity) may be able to help break tolerance to tumor antigens and improve cancer outcomes.

In the present disclosure, it is shown that pathogens and their components can augment an anti-tumor immune response within the tumor microenvironment, ultimately converting immunologically "cold" tumors to "hot." This results in inflammatory responses at the administration site that reduce local tumor growth, in augmented systemic anti-tumor immunity that decreases metastases, and in sensitization of resistant tumors to immune checkpoint blockade. Importantly, it has been demonstrated herein that such outcomes can be achieved by intratumoral, but not intramuscular, administration of vaccines.

BRIEF SUMMARY

Methods treating cancer are provided. The methods include intratumorally administering a therapeutically effective dose of a vaccine to a subject in need thereof.

BRIEF DESCRIPTION OF THE DRAWINGS

FIG. 1A-1G. Active influenza virus infection in the lung improves outcomes in mice and patients with tumors in the lung. (FIG. 1A) Experimental design. n=6-8 lung surfaces/group. Data are representative of at least two independent experiments with similar results. (FIG. 1B) Representative lung images showing melanoma foci from experiment described in (FIG. 1A). (C) Bar graph showing number of melanoma foci per lung surface from experiment described in (FIG. 1A). (FIG. 1D) Curves of lung cancer-specific mortality in patients with lung cancer included in the SEER-Medicare Linked Database and followed for 100 months, who had a recorded hospitalization for influenza virus infection (FLU dx) or not (No FLU dx) during the course of their lung cancer. n=34,277 patients. (FIG. 1E) As in (FIG. 1D), but assessing overall mortality. n=34,529 patients. (FIG. 1F) Bar graphs showing mean time to lung cancer-specific mortality in 25% of patients (P25) from database described in (FIG. 1D). (FIG. 1G) As in (FIG. 1F), but assessing overall mortality. *$P<0.05$, $P<0.01$, *$P<0.001$ [One-way ANOVA with Tukey correction (FIG. 1C), two-tailed student t test (FIG. 1F and FIG. 1G)]. Error bars: mean±s.e.m. i.v., intravenous. i.n., intranasal. i.p., intraperitoneal. PBS, phosphate-buffered saline. FLU-OVA, active influenza virus expressing SIINFEKL peptide (SEQ ID NO: 1) from ovalbumin (OVA$_{257-264}$). FLU, active influenza virus. IgG, control isotype antibody. αPD-1, PD-1 blocking antibody.

FIG. 2A-2H. Intratumoral heat-inactivated influenza virus administration reduces tumor growth in the skin and increases cross-presenting dendritic cells (DCs) and tumor antigen-specific CD8$^+$ T cells in the tumor. (FIG. 2A) Experimental design. n=4-5 mice per group. Data are representative of at least two independent experiments with similar results. (FIG. 2B) Tumor growth curves from experiment described in (FIG. 2A). (FIG. 2C) Survival curves from experiment described in (FIG. 2A). (FIG. 2D) Experimental design. n=3-5 tumors pooled/group. Data are representative of at least two independent experiments with similar results. (FIG. 2E) Cumulative pie charts of DCs (CD11c$^+$) among intratumoral antigen presenting cells (APCs, CD45$^+$MHC-II$^+$) from experiment described in (FIG. 2D). (FIG. 2F) Cumulative pie charts of cross-presenting dendritic cells (CD11c$^+$CD8a$^+$) among intratumoral APCs (CD45+MCH-II$^+$) from experiment described in (FIG. 2D). (FIG. 2G) Cumulative pie charts of CD8$^+$ T cells (CD8$^+$) among intratumoral T cells (CD45$^+$CD3$^+$) from experiment described in (FIG. 2D). (FIG. 2H) Cumulative flow cytometry plots of tumor antigen-specific CD8$^+$ T cells (TRP2-dextramer$^+$) among intratumoral CD8$^+$ T cells (CD45+CD3+CD8$^+$) from a similar experiment as described in (FIG. 2D). *P<0.05, ***P<0.001 [Two-way ANOVA with Bonferroni correction (FIG. 2B), Mantel-Cox log rank test (FIG. 2C)]. Error bars: mean±s.e.m. i.d., intradermal. i.t., intratumoral. PBS, phosphate-buffered saline. FLU-OVA, active influenza virus expressing SIINFEKL peptide (SEQ ID NO: 1) from ovalbumin (OVA$_{257-264}$). hiFLU-OVA, heat-inactivated influenza virus (hiFLU) expressing SIINFEKL peptide (SEQ ID NO: 1) from ovalbumin (OVA$_{257-264}$).

FIG. 3A-3I. Intratumoral unadjuvanted seasonal influenza vaccine administration reduces tumor growth, augments checkpoint blockade immunotherapy, and protects against active influenza virus lung infection. (FIG. 3A) Experimental design. Unadjuvanted seasonal influenza vaccine (FluVx): FluVx1. n=9 mice/group. Data are representative of at least two independent experiments with similar results. (FIG. 3B) Tumor growth curves from experiment described in (FIG. 3A). (FIG. 3C) Experimental design. FluVx: FluVx1. (FIG. 3D) Bar graphs showing count threshold (Ct) of active influenza virus (FLU) or GAPDH control qRT-PCR transcripts from experiment described in (FIG. 3C). (FIG. 3E) Experimental design. FluVx: FluVx1. n=4-5 mice/group. Data are representative of at least two independent experiments with similar results. (FIG. 3F) Tumor growth curves from experiment described in (FIG. 3E). (FIG. 3G) Schematic describing development of the autologous immune-reconstituted patient-derived xenograft (AIR-PDX) model in which NSG mice receive adoptive transfer of fresh patient-derived human peripheral blood mononuclear cells (PBMCs, 500,000 cells) and surgically implanted tumor sections (~5 mm×5 mm×3 mm) from the same (i.e., autologous) patient. FluVx: FluVx1. n=2-5 mice/group. (FIG. 3H) Bar graphs showing change in area of a primary lung tumor (day 13 area/day 0 area) from experiment described in (FIG. 3G). Dotted line corresponds to day 0 (first treatment day). (FIG. 3I) Bar graphs showing change in of a melanoma lymph node metastasis (day 16 area/day 0 area) from experiment described in (FIG. 3G). Dotted line corresponds to day 0 (first treatment day). *P<0.05, **P<0.01,

***P<0.001 [Two-way ANOVA with Bonferroni correction (FIG. 3B) or Tukey correction (FIG. 3F), two-tailed student t test (FIG. 3H and FIG. 3I). Error bars: mean±s.e.m. i.d., intradermal. i.t., intratumoral. i.p., intraperitoneal. i.n., intranasal. qRT-PCR, quantitative real-time polymerase chain reaction. PBS, phosphate-buffered saline. IgG, control isotype antibody. αPD-L1, PD-L1 blocking antibody.

FIG. 4A-4J. Intratumoral unadjuvanted seasonal influenza vaccine administration produces an immunologically "hot" tumor microenvironment and increases dendritic cells (DCs) and tumor antigen-specific CD8$^+$ T cells in the tumor. (FIG. 4A) Experimental design. Unadjuvanted seasonal influenza vaccine (FluVx): FluVx1. n=3-5 mice/group. Data are representative of at least two independent experiments with similar results. (FIG. 4B) Tumor growth curves from experiment described in (FIG. 4A). (FIG. 4C) Representative heatmap of a focused NanoString PanCancer Immune Profiling analysis of tumors 7 days post treatment. FluVx: FluVx1. (FIG. 4D) Experimental design. FluVx: FluVx2. n=3-5 tumors pooled/group. Data are representative of at least two independent experiments with similar results. (FIG. 4E) Cumulative pie charts of DCs (CD11c$^+$) among intratumoral antigen presenting cells (APCs; CD45$^+$ MHC-II$^+$) from experiment described in (FIG. 4D). (FIG. 4F) Cumulative pie charts of CD8$^+$ T cells (CD8$^+$) among intratumoral T cells (CD45$^+$CD3$^+$) from experiment described in (FIG. 4D). (FIG. 4G) Cumulative flow cytometry plots of tumor antigen-specific (gp100 dextramer$^+$) CD8$^+$ T cells among intratumoral CD8$^+$ T cells (CD45$^+$ CD3$^+$CD8$^+$) from a similar experiment as described in (FIG. 4D). (FIG. 4H) Scatter plot from T cell receptor (TCR) sequencing. FluVx: FluVx1. (FIG. 4I) Experimental design. FluVx: FluVx1. n=3-4 mice/group. (J) Tumor growth curves from experiment described in (I). *P<0.05, P<0.01, *P<0.001 [Two-way ANOVA with Tukey correction (FIG. 4B and FIG. 4J), two-tailed student t test (FIG. 4H)]. Error bars: mean±s.e.m. i.d., intradermal. i.t., intratumoral. i.p., intraperitoneal. PBS, phosphate-buffered saline. IgG, control isotype antibody. αCD8, CD8 depleting antibody.

Figures 5, 5A, 5B, 5C, 5D, 5E, 5F, 5G, 5H, 5I:
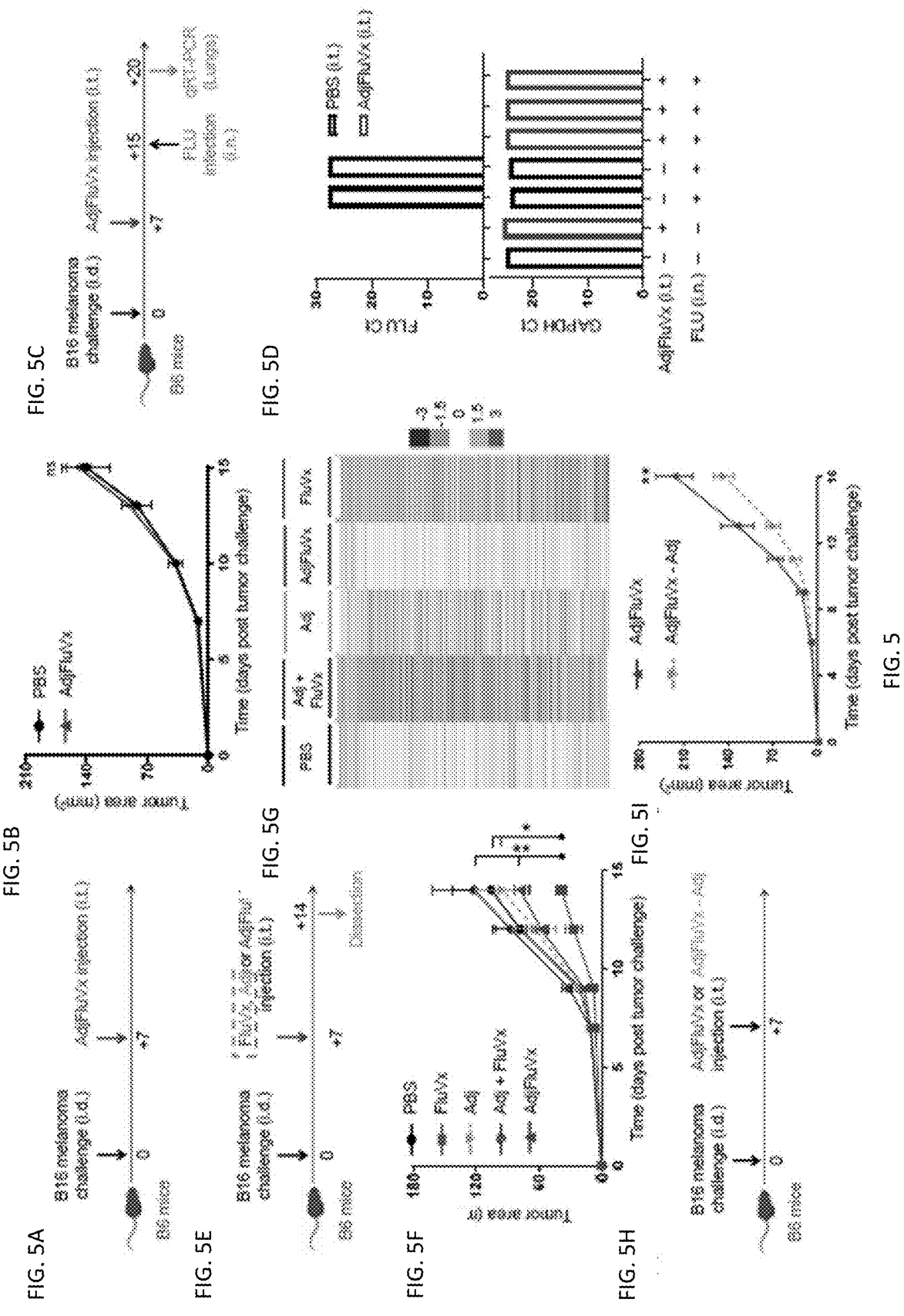

FIG. 5A-5I. Intratumoral "adjuvanted" seasonal influenza vaccine administration does not reduce tumor growth but does protect against active influenza virus infection and reduces tumor growth upon removal of its adjuvant. (FIG. 5A) Experimental design. n=9-10 mice/group. Data are representative of at least two independent experiments with similar results. (FIG. 5B) Tumor growth curves from experiment described in (FIG. 5A). (FIG. 5C) Experimental design. (FIG. 5D) Bar graphs showing count threshold (Ct) of active influenza virus (FLU) or GAPDH control qRT-PCR transcripts from experiment described in (FIG. 5C). (FIG. 5E) Experimental design. Unadjuvanted seasonal influenza vaccine (FluVx): FluVx1. n=3-4 mice/group. (FIG. 5F) Tumor growth curves from experiment described in (FIG. 5E). (FIG. 5G) Representative heatmap of NanoString PanCancer Immune Profiling analysis of tumors 7 days post treatment from experiment described in (FIG. 5E). (FIG. 5H) Experimental design. n=3 mice/group. (FIG. 5I) Tumor growth curves from experiment described in (FIG. 5H). ns, not significant, *P<0.05, **P<0.01 [Two-way ANOVA with Bonferroni correction (FIG. 5B and FIG. 5I) or Tukey correction (FIG. 5F). Error bars: mean±s.e.m. i.t., intradermal. i.t., intratumoral. i.n., intranasal. qRT-PCR, quantitative real-time polymerase chain reaction. PBS, phosphate-buffered saline. AdjFluVx, "adjuvanted" seasonal influenza vaccine. Adj, adjuvant. Adj+FluVx, Adj added to FluVx. AdjFluVx−Adj, AdjFluVx with Adj removed.

FIG. 6A-6K. Intratumoral "adjuvanted" seasonal influenza vaccine administration fails to increase T cells but maintains regulatory B cells in the tumor. (FIG. 6A) Experimental design. Unadjuvanted seasonal influenza vaccine (FluVx): FluVx2. n=3-5 pooled tumors/group. Data are representative of at least two independent experiments with similar results. (FIG. 6B) Cumulative pie charts of dendritic cells (CD11c$^+$) among intratumoral antigen presenting cells (APCs; CD45$^+$MHC-II$^+$) from experiment described in (FIG. 6A) and 5D. (FIG. 6C) Cumulative pie charts of CD8$^+$ T cells (CD8$^+$) among intratumoral T cells (CD45$^+$CD3$^+$) from experiment described in (FIG. 6A) and FIG. 5D. (FIG. 6D) Cumulative flow cytometry plots of tumor antigen-specific (gp100 dextramer$^+$) CD8$^+$ T cells among intratumoral CD8$^+$ T cells (CD45$^+$CD3$^+$CD8$^+$) from a similar experiment as described in (FIG. 6A). Cumulative pie charts of B cell (CD19$^+$) to T cell (CD3$^+$) ratio among intratumoral T and B cells (CD45$^+$CD3$^+$CD19$^+$) and CD45$^+$CD19$^+$ CD3$^+$) from experiment described in (FIG. 6A). (FIG. 6F) Cumulative pie charts showing ratio of regulatory B cells (Bregs; IL-10$^+$) among intratumoral B cells (CD45$^+$CD20$^+$) from experiment described in (FIG. 6A). (FIG. 6G) Cumulative pie charts of regulatory T cells (Tregs; FOXP3+) among intratumoral CD4+ T cells (CD45$^+$CD3$^+$CD4$^+$) from experiment described in (FIG. 6A). (FIG. 6H) Experimental design. n=3-4 mice/group. Data are representative of at least two independent experiments with similar results. (FIG. 6I) Tumor growth curves from experiment described in (FIG. 6H). (FIG. 6J) Experimental design. n=4-10 mice/group from two experiments with similar results. (FIG. 6K) Tumor growth curves from experiment described in (J). *P<0.05, P<0.01, *P<0.001 [Two-way ANOVA with Tukey correction (FIG. 6I and FIG. 6K)]. Error bars: mean±s.e.m. i.d., intradermal. i.t., intratumoral. PBS, phosphate-buffered saline. FluVx, unadjuvanted seasonal influenza vaccine. AdjFluVx, "adjuvanted" seasonal influenza vaccine.

FIG. 7A-7F. Intratumoral active influenza virus administration does not reduce melanoma growth in the skin or prolong host survival. (FIG. 7A) Experimental design. n=4-9 mice/group. Data are representative of at least two independent experiments with similar results. (FIG. 7B) Tumor growth curves from experiment described in (FIG. 7A). (FIG. 7C) Survival curves from experiment described in (FIG. 7A). (FIG. 7D) Experimental design, from experiment shown in FIG. 2A. n=4-5 mice/group. Data are representative of at least two independent experiments with similar results. (FIG. 7E) Tumor growth curves from experiment described in (FIG. 7D). (FIG. 7F) Survival curves from experiment described in (FIG. 7D). ns, not significant [Two-way ANOVA with Bonferroni correction (FIG. 7B, FIG. 7E), Mantel-Cox log rank test (FIG. 7C, FIG. 7F)]. Error bars: mean±s.e.m. i.d., intradermal. i.t., intratumoral. PBS, phosphate-buffered saline. FLU, active influenza virus.

FIG. 8A-8B. Heat-inactivated influenza virus administration increases TLR7 activity to a greater extent than active influenza virus administration. (FIG. 8A) Experimental design. Data are from one experiment run in triplicate wells and representative of at least two independent experiments with similar results. (FIG. 8B) TLR7 activity read at $OD_{620\ nm}$ from experiment described in (FIG. 8A). P<0.01,*P<0.001 [One-way ANOVA with Tukey correction]. Error bars: mean±s.e.m. TLR7: HEK-Blue-mTLR7 cell line expressing mouse TLR7. Null: parental HEK293 cell line not expressing TLR7. FLU, active influenza virus. hiFLU, heat-inactivated influenza virus. PBS, phosphate-buffered saline. Agonist: TLR 7 agonist, CL264.

Figure 9A:
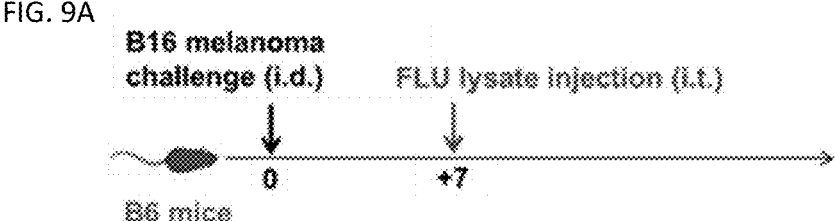
Figure 9B:
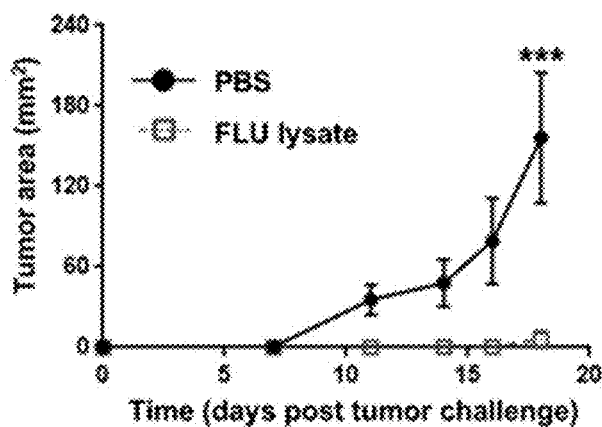

FIG. 9A-9B. Intratumoral influenza virus lysate administration reduces tumor growth in the skin. (FIG. 9A) Experimental design. n=5 mice/group. Data are representative of at least two independent experiments with similar results. (FIG. 9B) Tumor growth curves from experiment described in (FIG. 9A). ***P<0.001 [Two-way ANOVA with Bonferroni correction]. Error bar: mean±s.e.m. FLU lysate, influenza virus lysate. i.d., intradermal. i.t., intratumoral. PBS, phosphate-buffered saline.

Figure 10A:
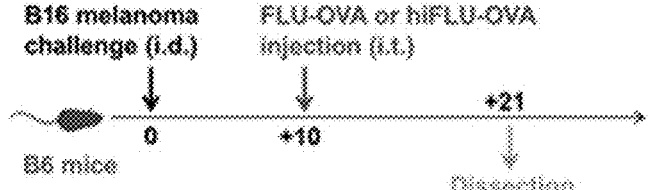
Figure 10B:
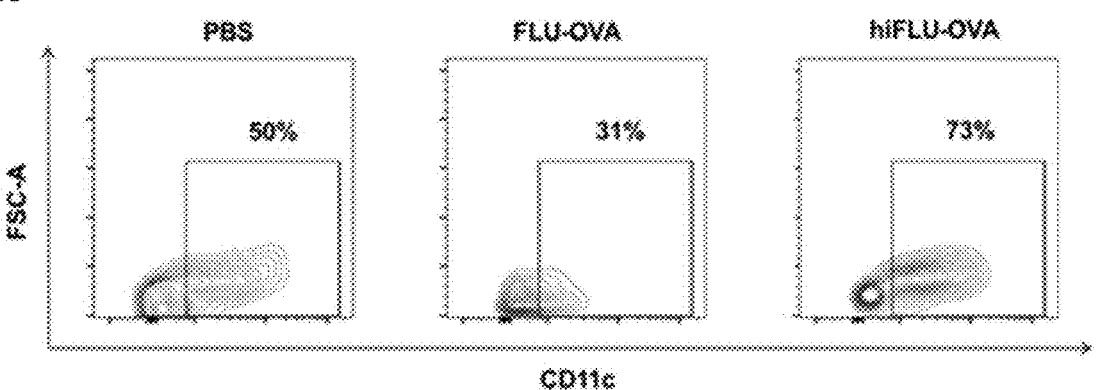
Figure 10C:
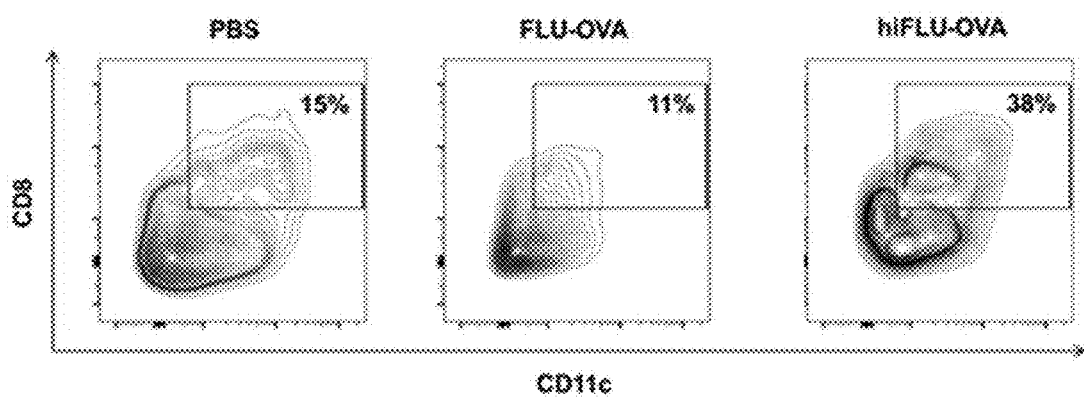

FIG. 10A-10C. Cumulative flow cytometry plots of intratumoral dendritic cells (DCs) from mice treated with FLU-OVA or hiFLU-OVA from experiment described in FIG. 2D-2F. (FIG. 10A) Experimental design. n=3-5 pooled tumors/group. Data are representative of at least two independent experiments with similar results. (FIG. 10B) Cumulative flow cytometry plots of DCs (CD11c$^+$) among intratumoral antigen-presenting cells (APCs, CD45$^+$MHC-II$^+$). (FIG. 10C) Cumulative flow cytometry plots of cross-presenting DCs (CD11c$^+$CD8$^+$) among intratumoral APCs (CD45$^+$MHC-II$^+$). i.d., intradermal. i.t., intratumoral. PBS, phosphate-buffered saline. FLU-OVA, active influenza virus expressing SIINFEKL peptide (SEQ ID NO: 1) from ovalbumin (OVA$_{257-264}$). hiFLU-OVA, heat-inactivated influenza virus expressing SIINFEKL peptide (SEQ ID NO: 1) from ovalbumin (OVA$_{257-264}$). FSC-A, forward scatter area.

FIG. 11A-11D. Intratumoral heat-inactivated influenza virus administration increases antigen presentation by dendritic cells (DCs) and requires cross-presenting DCs for tumor growth reduction. (FIG. 11A) Experimental design. n=3-5 pooled tumors/group. Data are representative of at least two independent experiments with similar results. (FIG. 11B) Cumulative flow cytometry plots of DCs presenting OVA$_{257-264}$ antigen (SIINFEKL(SEQ ID NO: 1)) within H-2Kb MHC-I molecule, H-2Kb-OVA (CD45$^+$ CD11c$^+$H-2Kb-OVA$^+$) among intratumoral DCs (CD45$^+$ CD11c$^+$) from experiment described in (FIG. 11A). (FIG. 11C) Experimental design. n=5 mice/group. (FIG. 11D) Tumor growth curves from experiment described in (FIG. 11C). ns, not significant [Two-way ANOVA with Tukey correction]. Error bars: mean±s.e.m. i.d., intradermal. i.t., intratumoral. PBS, phosphate-buffered saline. FLU-OVA, active influenza virus expressing SIINFEKL peptide (SEQ ID NO: 1) from ovalbumin (OVA$_{257-264}$). hiFLU-OVA, heat-inactivated influenza virus expressing SIINFEKL peptide (SEQ ID NO: 1) from ovalbumin (OVA$_{257-264}$). FSC-A, forward scatter area.

FIG. 12A-12B. Cumulative flow cytometry plots of intratumoral CD8$^+$ T cells from mice treated with FLU-OVA or hiFLU-OVA, from experiment described in FIGS. 2D and G. (FIG. 12A) Experimental design. n=3-5 pooled tumors/group. Data are representative of at least two independent experiments with similar results. (FIG. 12B) Cumulative flow cytometry plots of CD8$^+$ T cells (CD8$^+$) among intratumoral T cells (CD45$^+$CD3$^+$) for experiment descried in (FIG. 12A). i.d., intradermal. i.t., intratumoral. PBS, phosphate-buffered saline. FLU-OVA, active influenza virus expressing SIINFEKL peptide (SEQ ID NO: 1) from ovalbumin (OVA$_{257-264}$). hiFLU-OVA, heat-inactivated influenza virus expressing SIINFEKL peptide (SEQ ID NO: 1) from ovalbumin (OVA$_{257-264}$). FSC-A, forward scatter area.

Figure 13A:
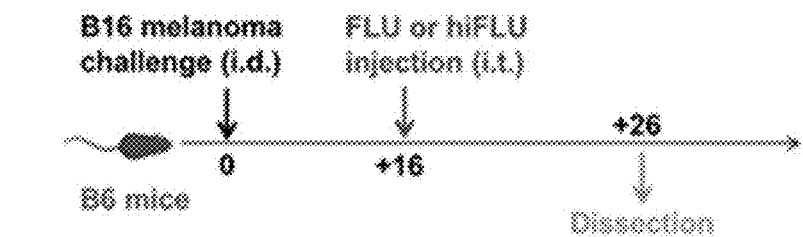
Figure 13B:
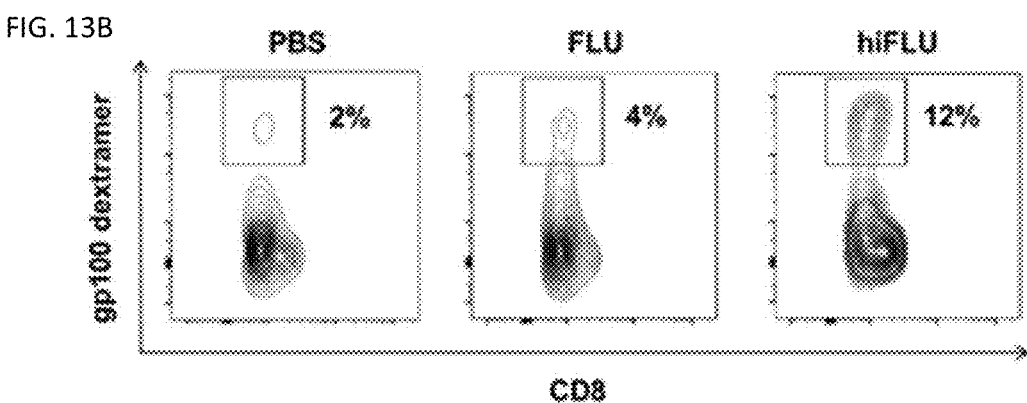

FIG. 13A-13B. Cumulative flow cytometry plots of intratumoral tumor antigen-specific CD8+ T cells from mice treated with FLU or hiFLU without OVA$_{257-264}$ peptide. (FIG. 13A) Experimental design. n=3-5 pooled tumors/group. (FIG. 13B) Cumulative flow cytometry plots of tumor antigen-specific (gp100-dextramer$^+$) CD8$^+$ T cells among intratumoral CD8$^+$ T cells from the experiment described in (FIG. 13A). i.d., intradermal. i.t., intratumoral. PBS, phosphate-buffered saline. FLU, active influenza virus. hiFLU.

Figures 14A, 14B, 14C, 14D, 14E, 14F, 14G, 14H, 14I, 14J, 14K:
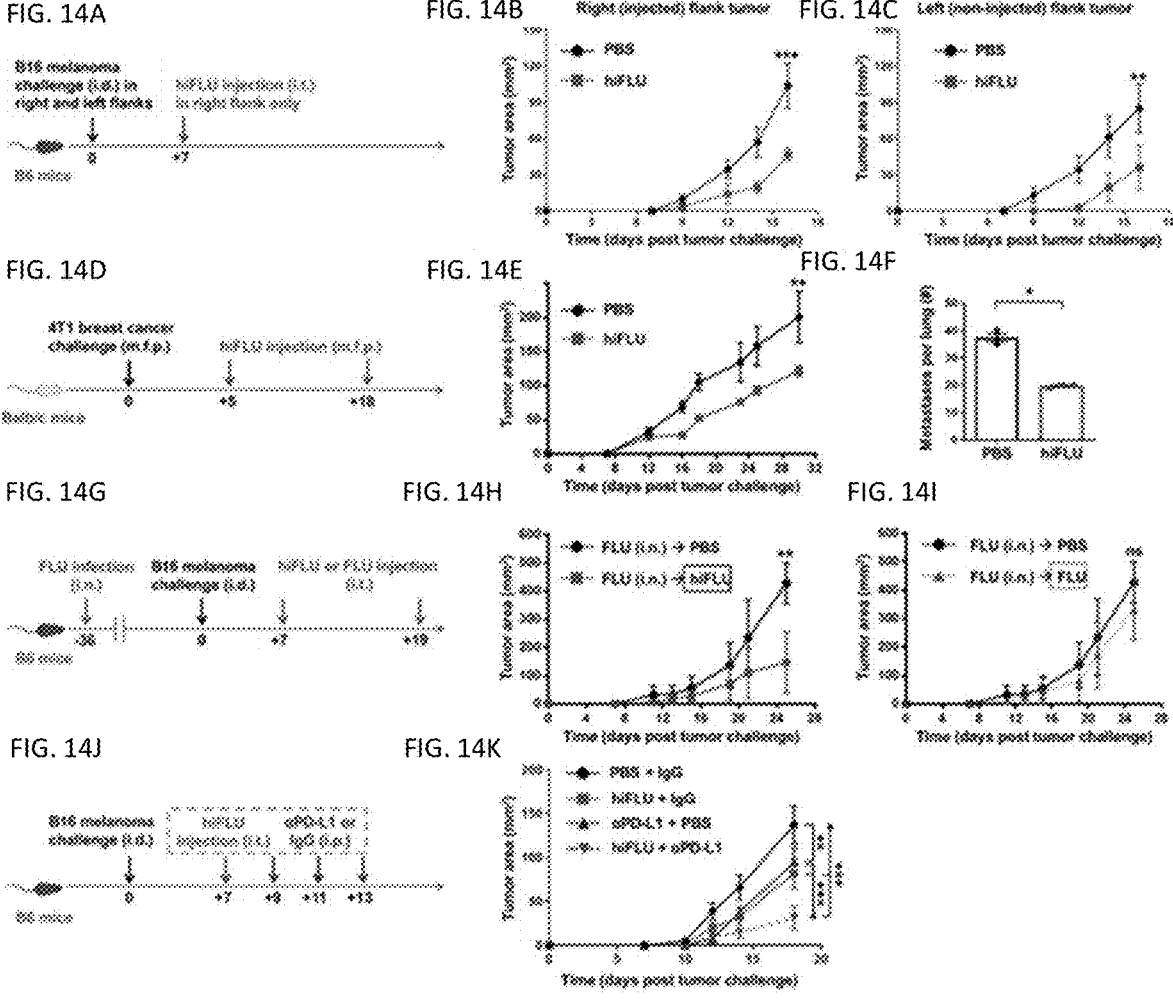

FIG. 14A-14K. Intratumoral heat-inactivated influenza virus administration reduces tumor growth systemically and in hosts previously infected with active influenza virus and augments responses to checkpoint blockade immunotherapy. (FIG. 14A) Experimental design. n=5-12 mice per group. (FIG. 14B) Tumor growth curves of right (injected) flank tumor from experiment described in (FIG. 14A). (FIG. 14C) Tumor growth curves of left (non-injected) flank tumor from experiment described in (FIG. 14A). (FIG. 14D) Experimental design. n=3-4 mice per group. (FIG. 14E) Tumor growth curves from experiment described in (FIG. 14D). (FIG. 14F) Bar graphs showing number of metastases per lung surface from experiment described in (FIG. 14D). (FIG. 14G) Experimental design. n=3 mice per group. (FIG. 14H) Tumor growth curves for mice infected with active influenza virus and subsequently administered hiFLU at the tumor site from experiment described in (FIG. 14G). (FIG. 14I) Tumor growth curves for mice infected with active influenza virus and subsequently administered FLU at the tumor site from experiment described in (FIG. 14G). (FIG. 14J) Experimental design. n=8-10 mice per group pooled from two similar experiments. (FIG. 14K) Tumor growth curves from experiments described in (FIG. 14J). ns, not significant, *P<0.05, P<0.01, *P<0.001 [Two-way ANOVA with Bonferroni correction (FIG. 14B, FIG. 14C, FIG. 14E, FIG. 14H, and FIG. 14I) or Tukey correction (FIG. 14K), two-tailed student t test (FIG. 14F)]. Error bars: mean±s.e.m. i.d., intradermal. i.t., intratumoral. m.f.p., mammary fat pad. i.n., intranasal. i.p., intraperitoneal. PBS, phosphate-buffered saline. FLU, active influenza virus. hiFLU, heat-inactivated influenza virus. IgG, control isotype antibody. aPD-L1, PD-L1 blocking antibody.

Figure 15A:
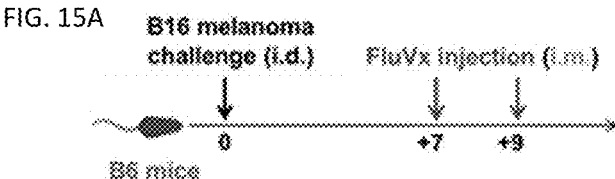
Figure 15B:
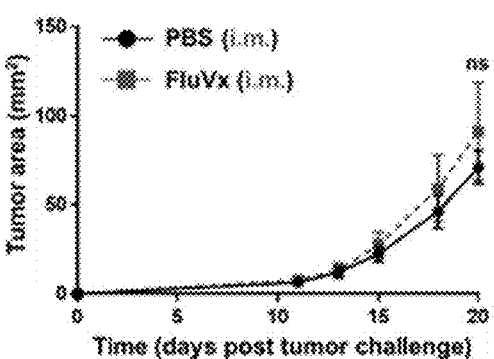

FIG. 15A-15B. Intramuscular unadjuvanted seasonal influenza vaccine administration does not reduce tumor growth in the skin. (FIG. 15A) Experimental design for intramuscular (i.m.) injection in the left lower limb). n=4-5 mice/group. Unadjuvanted seasonal influenza vaccine (FluVx): FluVx2. Data are representative of at least two independent experiments with similar results. (FIG. 15B) Tumor growth curves from experiment described in (FIG. 15A). ns=not significant [Two-way ANOVA with Bonferroni correction]. Error bars: mean±s.e.m. i.d., intradermal. PBS, phosphate-buffered saline.

Figure 16A:
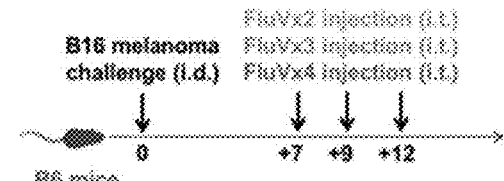
Figure 16B:
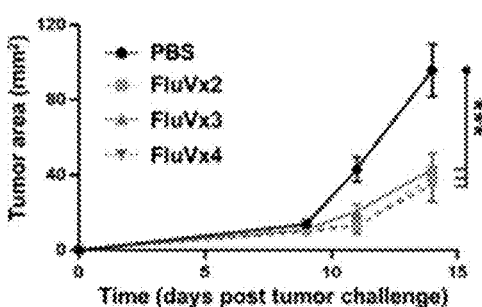
Figure 16C:
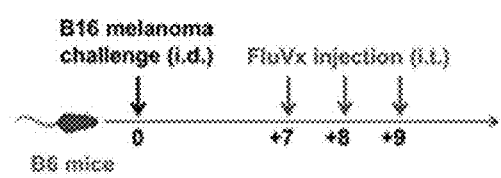
Figure 16D:
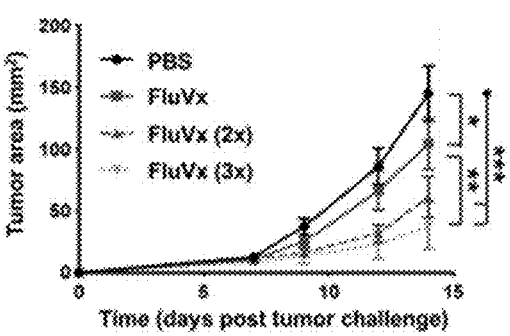

FIG. 16A-16D. Multiple 2017-2018 unadjuvanted seasonal influenza vaccines reduce tumor growth and intratumoral unadjuvanted seasonal influenza vaccination exhibits increased efficacy with multiple injections. (FIG. 16A) Experimental design for testing different unadjuvanted formulations of the seasonal influenza vaccine (FluVx): FluVx2, FluVx3, and FluVx4. These vaccines are defined in Table 1. n=4-5 mice/group. (FIG. 16B) Tumor growth curves from experiment described in (FIG. 16A). (FIG. 16C) Experimental design for studies utilizing one [day 7; 1×], two [days 7 and 8; 2×], or three [days 7, 8 and 9; 3×] injections. n=5-9 mice/group. FluVx: FluVx1. (D) Tumor growth curves from experiment described in (FIG. 16C). *P<0.05, P<0.01, *P<0.001 [Two-way ANOVA with Tukey correction (FIG. 16B and FIG. 16D)]. Error bars: mean±s.e.m. i.d., intradermal. i.t., intratumoral. PBS, phosphate-buffered saline.

FIG. 17A-17C. Cumulative flow cytometry plots of intratumoral dendritic cells (DCs) and CD8+ T cells from mice treated with unadjuvanted seasonal influenza vaccine, from experiment described in FIG. 4D-4F. (FIG. 17A) Experimental design. n=3-5 pooled tumors/group. Unadjuvanted seasonal influenza vaccine (FluVx): FluVx1. Data are representative of at least two independent experiments with similar results. (FIG. 17B) Cumulative flow cytometry plots of DCs (CD11c$^+$) among intratumoral antigen-presenting cells (APCs; CD45$^+$MHC-II$^+$) from experiment described in (FIG. 17A). (FIG. 17C) Cumulative flow cytometry plots of CD8+ T cells (CD8$^+$) among intratumoral T cells (CD45$^+$ CD3$^+$) from experiment described in (FIG. 17A). i.d., intradermal, i.t., intratumoral. PBS, phosphate-buffered saline. FSC-A, forward scatter area.

Figure 18A:
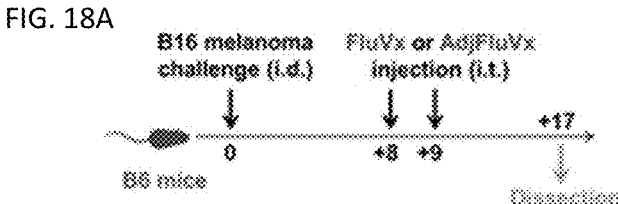
Figure 18B:
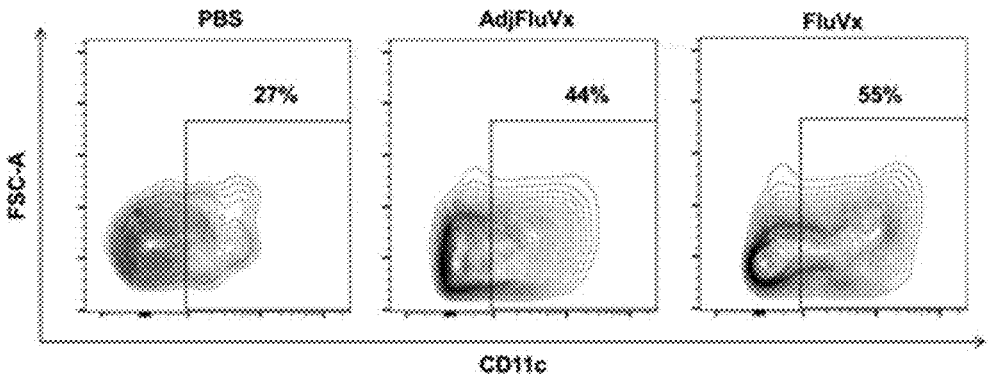
Figure 18C:
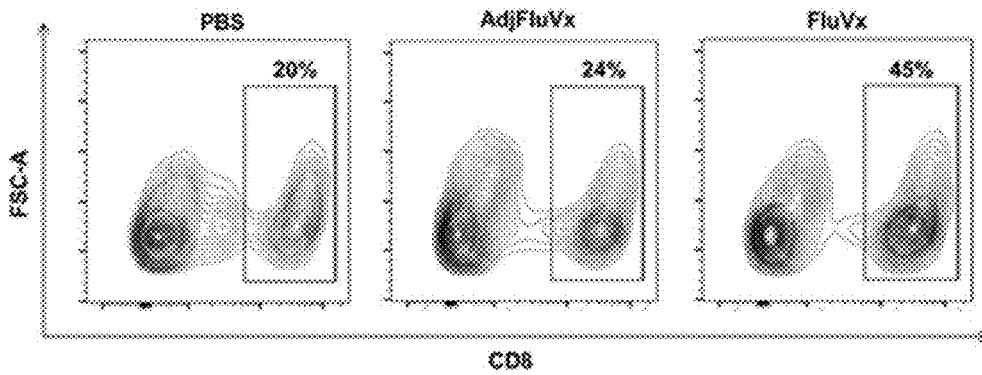
Figure 18D:
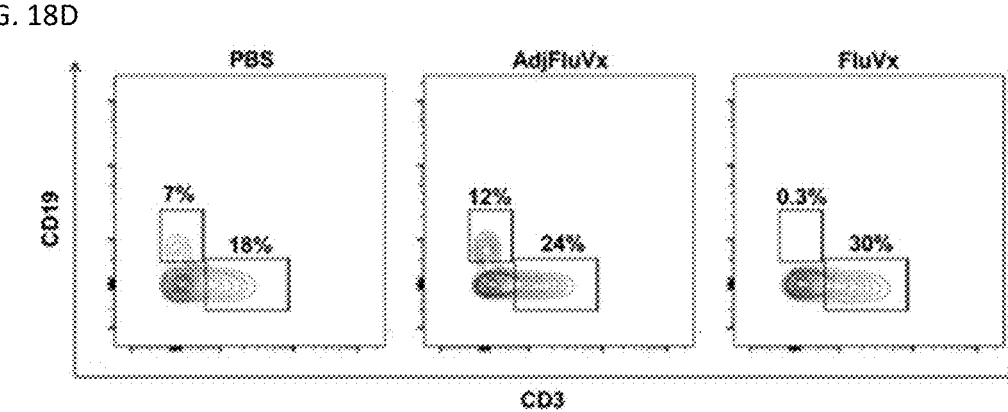

FIG. 18A-18D. Cumulative flow cytometry plots of intratumoral dendritic cells (DCs), CD8+ T cells, and ratio of B cells to T cells from mice treated with unadjuvanted or "adjuvanted" seasonal influenza vaccine, from experiment described in FIGS. 6A-6C and 6E. (FIG. 18A) Experimental design. Unadjuvanted seasonal influenza vaccine (FluVx): FluVx1. n=3-5 pooled tumors/group. Data are representative of at least two independent experiments with similar results. (FIG. 18B) Cumulative flow cytometry plots of dendritic cells (CD11c$^+$) among intratumoral antigen presenting cells (APCs; CD45$^+$MHC-II$^+$) from experiment described in (FIG. 18A). (FIG. 18C) Cumulative flow cytometry plots of CD8$^+$ T cells (CD8$^+$) among intratumoral T cells (CD45$^+$ CD3$^+$) from experiment described in (FIG. 18A). Cumulative flow cytometry plots of B cells (CD19$^+$) and T cells (CD3$^+$) among intratumoral immune cells (CD45$^+$) from experiment described in (A). i.d., intradermal, i.t., intratumoral. PBS, phosphate-buffered saline. FSC-A, forward scatter area. AdjFluVx, "adjuvanted" seasonal influenza vaccine.

Figure 19A:
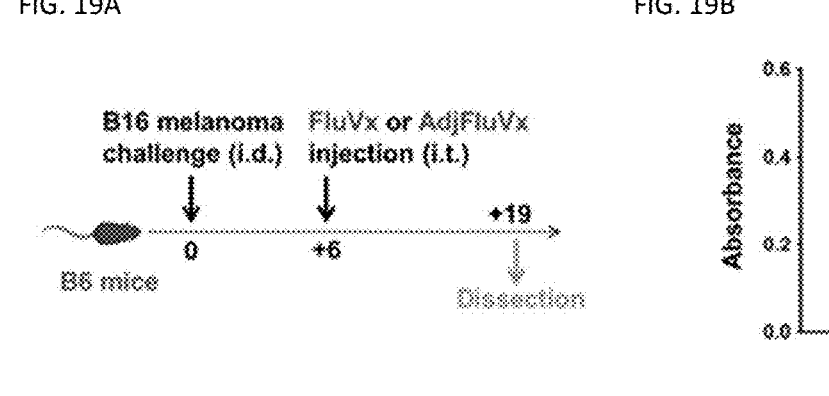
Figure 19B:
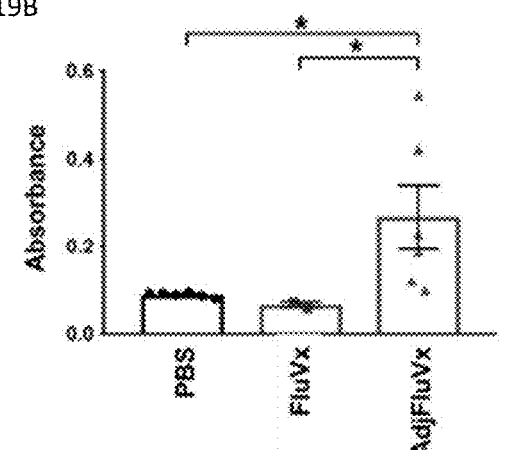

FIG. 19A-19B. Intratumoral adjuvanted seasonal influenza vaccine administration increases influenza virus-specific antibodies in the tumor. (FIG. 19A) Experimental design. Unadjuvanted seasonal influenza vaccine (FluVx): FluVx1. n=2-6 mice/group. Data are representative of at least two independent experiments with similar results. (FIG. 19B) Bar graphs showing absorbance measured by ELISA assay from experiment described in (FIG. 19A). *P<0.05 [Kruskal-Wallis with Dunn's Multiple Comparisons comparing all groups to AdjFluVx]. Error bars: mean±s.e.m. i.d., intradermal. i.t., intratumoral. AdjFluVx, "adjuvanted" seasonal influenza vaccine.

Figure 20A:
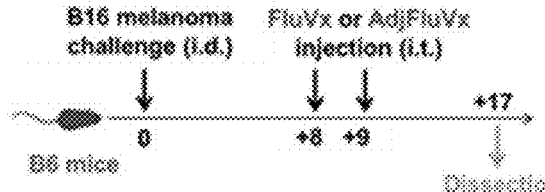
Figure 20B:
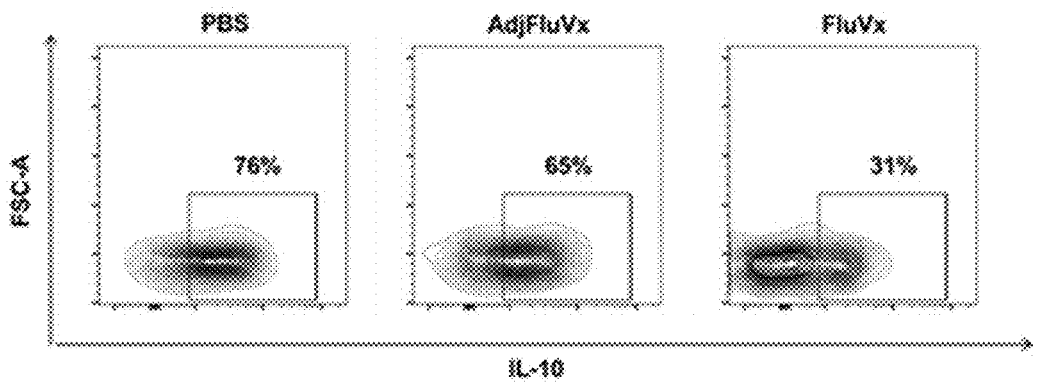
Figure 20C:
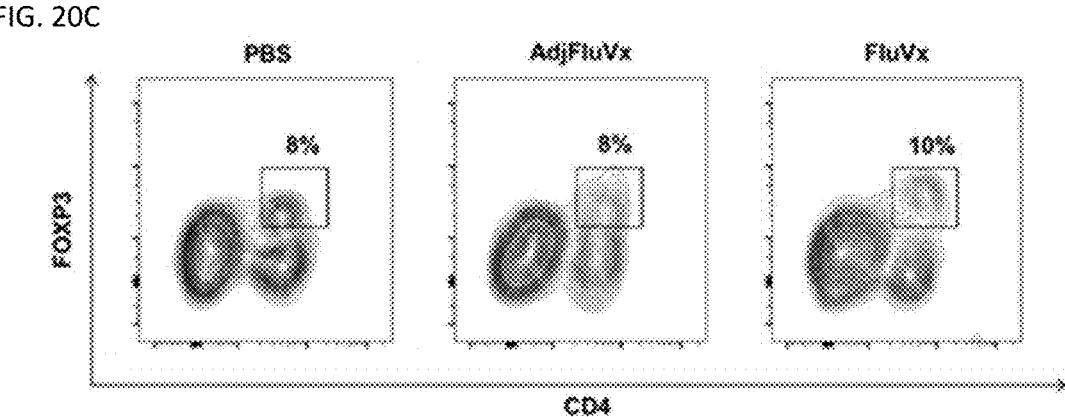

FIG. 20A-20C. Cumulative flow cytometry plots of intratumoral B regulatory cells and T regulatory cells from mice treated with unadjuvanted or "adjuvanted" seasonal influenza vaccine. (FIG. 20A) Experimental design. Unadjuvanted seasonal influenza vaccine (FluVx): FluVx1. n=3-5 pooled tumors/group. Data are representative of at least two independent experiments with similar results. (FIG. 20B) Cumulative flow cytometry plots of regulatory B cells (Bregs; IL-10$^+$) among intratumoral B cells (CD45$^+$CD20$^+$) from experiment described in (FIG. 20A). (FIG. 20C) Cumulative flow cytometry plots of regulatory T cells (Tregs; FOXP3$^+$) among intratumoral CD4+ T cells (CD45$^+$ CD3$^+$CD4$^+$) from experiment described in (A). i.d., intradermal. i.t., intratumoral. PBS, phosphate-buffered saline. FSC-A, forward scatter area. AdjFluVx, "adjuvanted" seasonal influenza vaccine.

FIG. 21A-21H. Multiple single and combination FDA-approved vaccines reduce tumor growth in multiple mouse tumor models and mouse strains. (FIG. 21A) Experimental design for testing FluVx1, DTaP diphtheria, tetanus, and pertussis), and Pneumovax (Pneumo) 13 days after tumor challenge (i.e., treatment day 0). n=3-5 mice/group. (FIG. 21B) Tumor growth curves from experiment described in (FIG. 21A). (FIG. 21C) Experimental design for testing combination (100 μl total) FluVx1, DTaP, and Pneumovax (Pneumo) 29 days after tumor challenge (i.e., treatment day 0). n=3-4 mice/group. (FIG. 21D) Tumor growth curves from experiment described in (FIG. 21C). (FIG. 21E) Experimental design for testing Pneumo, Hepatitis (HepB), DTaP, and FluVx1 seven days after tumor challenge. n=3-4 mice/group. (FIG. 21F) Tumor growth curves from experiment described in (FIG. 21E). (FIG. 21G) Experimental design for testing FluVx1, DTaP, measles/mumps/rubella (MMR), Pneumo, Hepatitis (HepB), DTaP, and FluVx2 seven days after tumor challenge. n=3-4 mice/group. (H) Tumor growth curves from experiment described in (G). *P<0.05, ***P<0.001 [Two-way ANOVA with Bonferroni correction for multiple comparisons (B, D, F, H)]. Error bars: mean±s.e.m. i.d., intradermal. i.t., intratumoral. PBS, phosphate-buffered saline.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings. Unless otherwise defined, all technical and scientific terms used herein have the same meaning as commonly understood by one of ordinary skill in the art to which this disclosure pertains. In case of conflict, the present document, including definitions, will control.

The uses of the terms "a" and "an" and "the" and similar references (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the disclosure and does not pose a limitation on the scope unless otherwise claimed. No language in the specification should be construed as indicating any non-claimed element as essential to the practice of the embodiments.

As used herein, the term "amount" refers to "an amount effective" or "therapeutically effective amount" of a composition, e.g., vaccine, to achieve a beneficial or desired prophylactic or therapeutic result, including clinical results. A "therapeutically effective amount" of a composition may vary according to factors such as the disease state, age, sex, and weight of the individual, and the ability of the composition to elicit a desired response in the individual. A therapeutically effective amount is also one in which any toxic or detrimental effects of the composition are outweighed by the therapeutically beneficial effects. The term "therapeutically effective amount" includes an amount that is effective to "treat" a subject (e.g., a patient). When a therapeutic amount is indicated, the precise amount of the compositions of the present disclosure to be administered may be determined by a physician with consideration of individual differences in age, weight, tumor size, extent of infection or metastasis, and condition of the patient (subject).

Influenza Vaccines

Influenza vaccines suitable for use herein may be any influenza vaccine derived from an influenza virus. The influenza vaccines may be FDA approved influenza vaccines or any other influenza vaccines that are directed to one or more antigens of the influenza virus. The influenza vaccines may be unadjuvanated where an additional adjuvant is not added to the vaccine after the vaccine is made but still includes the natural adjuvants that are part of the preparation of the vaccine itself. For example host cell proteins are considered to be part of an unadjuvanted vaccine. Human influenza virus strains for use in vaccines change from season to season. In the current inter-pandemic period, vaccines typically include two influenza A strains (H1N1 and H3N2) and one influenza B strain, and trivalent vaccines are typical. The influenza vaccine as used herein may also use HA from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the influenza vaccine may protect against one or more of HA subtypes H1, H2, H3, H4, H5, H6, H7, H8, H9, H10, H11, H12, H13, H14, H15 or H16 (influenza A virus). The influenza vaccine may protect against one or more of influenza A virus NA subtypes N1, N2, N3, N4, N5, N6, N7, N8 or N9.

Additional Vaccines

In some embodiments, the vaccine used may be other than an influenza vaccine. In some embodiments, the vaccine may be inactivated or live attenuated vaccines and may be an FDA-approved vaccine. In some embodiments, the vaccine may be selected from the group including DTaP (diphtheria, pertussis and tetanus), Pneumovax (Pneumococcal Pneumonia), HepB (hepatitis B), and MMR (measles, mumps, rubella) vaccines, but not limited thereto.

Compositions of the influenza vaccine as used herein may include antigen(s) from one or more (e.g. 1, 2, 3, 4 or more) influenza virus strains, including influenza A virus and/or influenza B virus. Exemplary FDA approved influenza vaccines for the 2017-2018 flu season are shown in Table 1. Compositions as used herein may include a vaccine other than an influenza vaccine. Monovalent vaccines can be prepared, as can 2-valent, 3-valent, 4-valent, etc.

In some embodiments, the vaccine may include an adjuvant that is non B-cell promoting. In some embodiments, the vaccine may include an adjuvant. If the adjuvant is B-cell promoting, a treatment may be given so that B-cells may be decreased intratumorally. In some embodiments, IL-10 expression may be decreased.

Intratumoral Administration

To perform the treatment described herein, a vaccine as described herein can be administered to a subject in need of the treatment via a suitable route such as intratumoral administration. The term "intratumoral administration" refers to the delivery of a composition into or adjacent to a tumor or cancer and/or immediate vicinity of a tumor or cancer. Multiple injections into separate regions of the tumor or cancer are also included. Furthermore, intratumoral administration includes delivery of a composition into one or more metastases.

Methods for intratumoral delivery of drugs are known in the art (Brincker, 1993. Crit. Rev. Oncol. Hematol. 15(2): 91-8; Celikoglu et al., 2008. Cancer Therapy 6, 545-552).

For example, the composition can be administered by conventional needle injection, needle-free jet injection or electroporation or combinations thereof into the tumor or cancer tissue. The composition can be administered directly into the tumor or cancer (tissue) with great precision using computer tomography, ultrasound, gamma camera imaging, positron emission tomography, or magnetic resonance tumor imaging. Further procedures are selected from the group including, but not limited to, direct intratumoral administration by endoscopy, bronchoscopy, cystoscopy, colonoscopy, laparoscope and catheterization. In some embodiments where the tumor is in contact with bodily fluid in a closed system, the composition may be administered to the fluid for intratumoral administration. Non-limiting examples include administration to the spinal column to treat a tumor in the brain or intravesicular administration to the bladder.

In some embodiments, the vaccines described herein may be used to treat disorders that include, but are not limited to the following: melanoma, non-small cell lung, small-cell lung, lung, hepatocarcinoma, retinoblastoma, astrocytoma, glioblastoma, leukemia, neuroblastoma, head, neck, breast, pancreatic, prostate, renal, bone, testicular, ovarian, mesothelioma, cervical, gastrointestinal, urogenital, respiratory tract, hematopoietic, musculoskeletal, neuroendocrine, carcinoma, sarcoma, central nervous system, peripheral nervous system, lymphoma, brain, colon or bladder cancer. In some embodiments, the vaccines are not used to treat melanoma. In some embodiments the vaccines may be used with any solid tumor that is accessible for intratumoral administration.

The intratumoral administration may be used to accomplish one or more of the following: (a) reducing tumor size; (b) reducing tumor growth; (c) reducing or limiting development and/or spreading of metastases; (d) eliminating a tumor; (e) inhibiting, preventing, or reducing the recurrence of a tumor for at least 3 months, at least 6 months, or at least 12 months, (f) promoting an immune response against a tumor. The effect may be found in the tumor to which the vaccine was administered and/or one or more metastases or other tumor.

Checkpoint Blockade Immunotherapy

In some embodiments, the vaccine may be used in combination with an immune checkpoint inhibitor. Immune checkpoints are molecules in the immune system that either turn up a signal (co-stimulatory molecules) or turn down a signal. Many cancers protect themselves from the immune system by inhibiting the T cell signal. An immune checkpoint inhibitor can help stop such a protective mechanism by the cancer cells. An immune checkpoint inhibitor may target any one or more of the following checkpoint molecules, Programmed T cell death 1 (PD-1), programmed T cell death ligand 1 (PD-L1) (also known as CD279), PD-L2, Cytotoxic T-lymphocyte antigen 4 (CTLA-4) (also known as CD152) (CTLA-4), Lymphocyte-activation gene 3 (LAG-3) (also known as CD223), T-cell immunoglobulin and mucin-domain containing-3 (Tim-3), CD28, CD122, or 4-1 BB (also known as CD137).

PD-1 is a trans-membrane protein found on the surface of T cells, which, when bound to PD-L1 or PD-L2 on tumor cells or immune cells, results in suppression of T cell activity and reduction of T cell-mediated cytotoxicity. PD-1 and PD-L1 are immune down-regulators or immune checkpoint "off switches". Examples of PD-1 inhibitors include, but are not limited to, nivolumab, (Opdivo) (BMS-936558), pembrolizumab (Keytruda), pidilizumab, AMP-224, MED10680 (AMP-514), PDR001, MPDL3280A, MEDI4736, BMS-936559 and MSB0010718C. Examples of PD-L1 inhibitors include Atezolizumab (Tecentriq), Durvalumab (MED14736), Avelumab (MSB0010718C), MPDL3280A, BMS935559 (MDX-1105) and AMP-224, but are not limited thereto.

CTLA-4 is a protein receptor that downregulates the immune system. Non-limiting examples of CTLA-4 inhibitors include ipilimumab (Yervoy) (also known as BMS-734016, MDX-010, MDX-101) and tremelimumab (formerly ticilimumab, CP-675,206).

LAG-3 is an immune checkpoint receptor on the cell surface works to suppress an immune response by action to Tregs as well as direct effects on CD8$^+$ T cells. LAG-3 inhibitors include, but are not limited to, LAG525 and BMS-986016.

CD28 is constitutively expressed on almost all human CD4$^+$ T cells and on around half of all CD8 T cells. prompts T cell expansion. A non-limiting example of a CD28 inhibitor is TGN1412.

CD122 increases the proliferation of CD8$^+$ effector T cells. A non-limiting example of a CD122 inhibitor is NKTR-214.

CD137 is involved in T-cell proliferation. CD137-mediated signaling is also known to protect T cells, and in particular, CD8$^+$ T cells from activation-induced cell death. Non-limiting examples of CD137 inhibitors include PF-05082566, Urelumab (BMS-663513) and lipocalin.

As used herein, the term "checkpoint inhibitor" refers to any molecules, including antibodies, fragments thereof and small molecules, that block the immunosuppression pathway induced by one or more checkpoint molecules.

Pharmaceutical Compositions

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al, (2003) New Engl. J. Med. 348:601-608; Milgrom et al, (1999) New Engl. J. Med. 341: 1966-1973; Slamon et al, (2001) New Engl. J. Med. 344:783-792; Beniaminovitz et al, (2000) New Engl. J. Med. 342:613-619; Ghosh et al, (2003) New Engl. J. Med. 348:24-32; Lipsky et al, (2000) New Engl. J. Med. 343: 1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts. Compositions comprising vaccines can be provided by continuous infusion, or by doses at intervals of, e.g., one day, one week, or 1-7 times per week intratumorally. In some embodiments, a single dose or multiple doses of the vaccine may be administered intratumorally. In some embodiments, dosing of the composition may be weekly or every other week or every two to three weeks. Doses of additional therapeutics may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05µ/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, at least 30 mg/kg, at least 40 mg/kg or at least 50 mg/kg (see, e.g., Yang et al, (2003) New Engl. J. Med. 349:427-434; Herold et al, (2002) New Engl. J. Med. 346: 1692-1698; Liu et al, (1999) J. Neurol. Neurosurg. Psych. 67:451-456; Portielji et al, (2003) Cancer Immunol. Immunother. 52: 133-144).

An effective amount for a particular patient may vary depending on factors such as the condition being treated, the overall health of the patient, the method route and dose of administration and the severity of side effects (see, e.g., Maynard et al., (1996) A Handbook of SOPs for Good Clinical Practice, Interpharm Press, Boca Raton, Fla.; Dent (2001) Good Laboratory and Good Clinical Practice, Urch PubL, London, UK).

The route of administration for the vaccine may be intratumoral administration or any non-intramuscular route. The route of administration for additional therapeutic agents may be by, e.g., topical or cutaneous application, injection or infusion by intravenous, intraarticular, intraperitoneal, intracerebral, intramuscular, intraocular, intraarterial, intracerebrospinal, intralesional, or by sustained release systems or an implant (see, e.g., Sidman et al., (1983) Biopolymers 22:547-556; Langer et al., (1981) J. Biomed. Mater. Res. 15: 167-277; Langer (1982) Chem. Tech. 12:98-105; Epstein et al, (1985) Proc. Natl. Acad. Sci. USA 82:3688-3692; Hwang et al., (1980) Proc. Natl. Acad. Sci. USA 77:4030-4034; U.S. Pat. Nos. 6,350,466 and 6,316,024). In some embodiments, the vaccine may be administered by any non-intramuscular route, including but not limited to topical or cutaneous application, injection or infusion by intravenous, intraarticular, intraperitoneal, intracerebral, intraocular, intraarterial, intracerebrospinal, intralesional, or by sustained release systems or an implant. Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

Methods for co-administration or treatment with a second therapeutic agent, e.g., an antibody or chemotherapeutic agent, by way of non-limiting example, are known in the art (see, e.g., Hardman et al., (eds.) (2001) Goodman and Gilman's The Pharmacological Basis of Therapeutics, IO.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%>; at least 40%>, or at least 50%.

Additional therapies (e.g., prophylactic or therapeutic agents), which can be administered in combination with the agent described herein may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the vaccine. The two or more therapies may be administered within one same patient visit.

The vaccine and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the therapeutic agents can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes or nanoparticles. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al); mannosides (Umezawa et al, (1988) Biochem. Biophys. Res. Commun. 153: 1038); antibodies (Bloeman et al, (1995) FEBS Lett. 357: 140; Owais et al., (1995) Antimicrob. Agents Chemother. 39: 180); surfactant protein A receptor (Briscoe et al, (1995) Am. J. Physiol. 1233: 134); p 120 (Schreier et al, (1994) J. Biol. Chem. 269:9090); see also K. Keinanen; M. L. Laukkanen (1994) FEBS Lett. 346: 123; J. J. Killion; I. J. Fidler (1994) Immunomethods 4:273.

The therapies (e.g., prophylactic or therapeutic agents) of the combination therapies can be administered to a subject concurrently. The term "concurrently" is not limited to the administration of therapies (e.g., prophylactic or therapeutic agents) at exactly the same time, but rather it is meant that a pharmaceutical composition comprising a vaccine are administered to a subject in a sequence and within a time interval such that the vaccine can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Results

Active influenza virus infection in the lung improves outcomes in mice and patients with tumors in the lung Reports describing cancer outcomes in the context of infection have been discordant (18-21). We recently reported that active influenza virus infection in the lung accelerates early melanoma growth in the skin (22). Further, we showed that anti-tumor CD8$^+$ T cells are shunted from the tumor site (skin) to the distant infection site (lung), resulting in decreased immunity within the tumor, thus permitting accelerated tumor growth (22). Based on these findings and inspired by the previous work of others demonstrating improved anti-cancer outcomes by targeting pathogens to tumors (23-27), we hypothesized that infection in the same tissue as the tumor (even if the pathogen were not infecting tumor cells directly) would shunt immune cells to this "shared" site of infection and tumor, and thus inflame the tumor microenvironment to reduce tumor growth and prolong host survival. To test our hypothesis, we utilized the same tumor and infection models as our previous report (22), but here, challenged C57BL/6J (B6) mice with B16-F10 melanoma via intravenous injection to localize the tumor to the lung. Concurrently, we administered intranasal injection of active influenza A/PR8/1934/H1N1 virus expressing OVA$_{257-264}$ peptide, SIINFEKL (FLU-OVA) (SEQ ID NO: 1) to create a productive infection in the lung (i.e., the same tissue as the tumor). Indeed, active influenza virus infection in the lung reduced melanoma foci in the lung, and this effect was augmented in combination with PD-1 checkpoint blockade (FIGS. 1A and 1B). To determine whether our findings have corresponding clinical relevance, we surveyed the SEER-Medicare Linked Database of over 30,000 patients with lung cancer. We found that patients who had one or more diagnoses of influenza virus infection during their lung cancer course exhibited decreased lung cancer-specific and overall mortality (FIGS. 1C and 1D), in agreement with our mouse model observations. Importantly, the time to lung cancer-specific mortality and overall mortality in 25% of each population was prolonged 12 and 19 months, respectively, for patients with one or more diagnoses of influenza virus infection during their lung cancer course (FIGS. 1E and 1F).

Intratumoral heat-inactivated, but not active, influenza virus administration reduces tumor growth in the skin Since we determined that active influenza virus administration in the lung reduces melanoma tumors in the lung, and since melanomas form most frequently in the skin, we sought to translate our findings to this more prevalent site. However, intratumoral injection of active influenza virus did not alter skin melanoma growth or host survival (FIG. 7). We hypothesized that since the skin lacks the natural targets for active influenza virus infection that are present in the lung, such virus injected into the skin may be cleared without productive infection of cells within the skin. In this situation, pathways of immune activation including toll-like receptor (TLR)-mediate pathways that are otherwise initiated by the recognition of pathogen-associated molecular patterns (PAMPs) may not be engaged. Further, studies have shown that active influenza virus injection in the skin dysregulates dendritic cells (DCs) (28). To bypass these scenarios, we created inactivated versions of our active influenza via heat inactivation and chemical lysis. Indeed, when compared to active influenza virus, a heat-inactivated version of our A/PR8/1934/H1N1 active influenza virus (hereafter referred to as, hiFLU), demonstrated augmented TLR7 activity, which is produced in response to ssRNA, a natural agonist that constitutes influenza virus (FIG. 8). Importantly, intratumoral administration of hiFLU (or influenza lysate [FLU lysate] likewise derived from active influenza A/PR8/1934/H1N1 virus) reduced tumor growth and prolonged host survival (FIG. 2A-2C, FIG. 9). Intratumoral hiFLU administration also increased DCs among antigen presenting cells (APCs) in the tumor and, specifically, cross-presenting CD8$^+$ DCs (FIG. 2D-2F, SI FIG. 10A-C) that have been shown to be important in anti-tumor and anti-pathogen (including oncolytic virus) immune responses (29, 30). Further, heat-inactivated influenza virus increased antigen presentation by DCs within the tumor, as demonstrated utilizing hiFLU-OVA, and identifying (via an H-2Kb-OVA antibody) cells presenting SIINFEKL (SEQ ID NO: 1) within B6 mouse MHC class I molecule, H-2Kb (FIGS. 11A and 11B). In Batf3$^{-/-}$ mice, which lack cross-presenting DCs (29), intratumoral hiFLU-OVA had no effect on tumor growth, thus demonstrating their necessity (FIGS. 11C and 11D). Consistent with these findings, we observed increased intratumoral CD8$^+$ T cells, and importantly, anti-tumor CD8$^+$ T cells within the tumor microenvironment after hiFLU or hiFLU-OVA administration (FIGS. 2G and 2H, FIG. 12, FIG. 13). These findings demonstrate that an inactivated influenza virus can be utilized in the context of the tumor microenvironment to augment an anti-tumor immune response.

Heat-inactivated influenza virus promotes systemic anti-tumor immunity, reduces tumor growth in hosts previously infected with active lung influenza virus, and augments checkpoint blockade immunotherapy To determine whether the sum of the mechanistic changes we observed with intratumoral heat-inactivated injection provides systemic immunity, we conducted a bilateral flank experiment. Indeed, both the hiFLU-treated (injected) right and untreated (non-injected) left flank tumors exhibited reduced melanoma growth (FIG. 14A-14C), suggesting that local intratumoral hiFLU augments systemic anti-tumor responses. A similar systemic outcome was observed in the 4T1 model of metastatic triple-negative breast cancer, where both primary tumor growth and lung metastases were reduced after intratumoral injection of hiFLU only into the primary tumor (FIG. 14D-14F), suggesting that intratumoral hiFLU positive anti-tumor outcomes are not limited to skin cancers or to non-metastatic tumors. Importantly, intratumoral hiFLU similarly decreased melanoma growth in hosts previously infected with influenza virus (FIG. 14G-14I), suggesting that intratumoral hiFLU as a treatment for cancer may be utilized in hosts that have been previously infected by and have cleared the same pathogen. To determine whether intratumoral hiFLU could augment checkpoint blockade immunotherapy, hiFLU and PD-L1 blockade were administered in combination. Combination treatment with PD-L1 checkpoint blockade in the melanoma model further reduced tumor growth, compared to that observed with either hiFLU or PD-L1 blockade alone (FIGS. 14J or and 14K). This suggests that patients who respond (even partially) to such checkpoint blockade may benefit further from administration of intratumoral heat-inactivated influenza virus.

Unadjuvanted seasonal influenza vaccine administered via intratumoral injection reduces growth of mouse and human cancers and makes resistant tumors responsive to checkpoint blockade immunotherapy Based on the successes of the inactivated influenza viruses (that we produced from active influenza virus) for reducing tumor growth, and with clinical translatability in mind, we hypothesized that commercially available seasonal influenza vaccines ("flu shots") could be repurposed for cancer immunotherapy, as the majority of these vaccines are inactivated like the hiFLU we produced. Indeed intratumoral, but not intramuscular, injection of 2017-2018 unadjuvanted seasonal influenza vaccine (FluVx, Table 1) resulted in reduced tumor growth (FIGS. 3A and 3B, FIG. 15, FIGS. 16A and 16B). Multiple FluVx administrations further reduced tumor growth (FIGS. 16C and 16D), suggesting a role here for the prime-boost approach used for children receiving their initial influenza vaccination. Other vaccines, both inactivated and live attenuated, likewise reduced tumor growth (FIG. 21A-21H), including DTaP, Pneumovax (Pneumo), Hepatitis B (HepB), and combination FluVx1/DTaP/Pneumovax, in one or more cancer types (melanoma and/or colon carcinoma) and mouse strains (C57BL/6 and/or Balb/C).

Importantly, intratumoral injection of FluVx afforded hosts protection against subsequent active influenza virus infection (FIGS. 3C and 3D), suggesting that administration of an unadjuvanted seasonal influenza vaccine in the tumor may be used to simultaneously reduce tumor growth and provide vaccination-induced protection against influenza virus lung infection. The combination of FluVx with PD-L1 checkpoint blockade further reduced tumor growth, even in the context where the tumor was resistant to checkpoint blockade alone (FIGS. 3E and 3F). To gauge the possible effect of intratumoral FluVx administration on patient tumors, we utilized the autologous immune-reconstituted patient-derived xenograft (AIR-PDX) mouse model that we have developed. AIR-PDX mice harbor surgically transplanted patient tumor tissue (thus, maintaining the natural architecture of the patient's tumor) and adoptively transplanted peripheral blood immune cells from the same (autologous) patient (FIG. 3G) (thus not requiring stem cells and avoiding mismatched immunity in the tumor versus peripheral blood and tissues). In this model, intratumoral FluVx likewise reduced growth of a patient-derived primary lung tumor and patient-derived melanoma lymph node metastasis (FIGS. 3H and 3I), suggesting the translatability of our findings to clinical cancer treatment.

Intratumoral unadjuvanted seasonal influenza vaccine increases the proportion of intratumoral dendritic cells and tumor antigen-specific CD8$^+$ T cells within the tumor microenvironment Towards defining mechanisms underlying our FluVx findings, we determined the contribution of the immune system to our observed outcomes. In NOD scid gamma (NSG) mice, which lack a functional immune system (31), FluVx had no effect on tumor growth; however, immune reconstitution of NSG mice via adoptive cell transfer of splenic-derived immune cells fully recovered the anti-tumor effect of FluVx (FIGS. 4A and 4B), suggesting that the immune system is required for FluVx's ability to reduce tumor growth. A focused analysis of inflammation-related mRNAs previously shown to correlate with clinical response in patients to PD-1 checkpoint blockade (5) demonstrated high expression of such mRNAs with intratumoral FluVx administration (FIG. 4C), suggesting conversion of an immunologically "cold" tumor to "hot." As with hiFLU, we observed with FluVx an increase in DCs among all APCs in the tumor and a corresponding increase in intratumoral CD8$^+$ T cells (FIG. 4D-4F, FIG. 17). Importantly, among CD8$^+$ T cells, we observed an increase in tumor antigen-specific CD8$^+$ T cells (FIG. 4G), suggesting that intratumoral anti-pathogen vaccination boosts tumor-specific immunity. Consistent with these findings, and further suggesting that FluVx augments anti-tumor T cell responses, T cell receptor (TCR) sequencing demonstrated an increase in the representation of tumor-associated clones (i.e., increased evenness/clonality) with intratumoral FluVx (FIG. 4H), a therapy-induced change previously reported in patients responding to PD-1 checkpoint blockade (32). Importantly, depletion of CD8-expressing cells completely abrogated the FluVx anti-tumor effect (FIGS. 4I and 4J), demonstrating the importance of such cells in the underlying immune mechanism of FluVx.

A seasonal influenza vaccine that is "adjuvanted" fails to reduce tumor growth due to maintenance of regulatory B cells While all tested unadjuvanted influenza vaccines resulted in improved anti-tumor outcomes, an available "adjuvanted" formulation (hereafter referred to as AdjFluVx, Table 1) demonstrated no tumor-reduction effect (FIGS. 5A and 5B). We recognized this difference between the unadjuvanted and "adjuvanted" formulation as a unique opportunity to uncover additional mechanisms that drive tumor regression versus progression. Importantly, AdjFluVx, which has been demonstrated in clinical trials to afford anti-influenza virus protection (particularly in patients over 65 years old) (33, 34), did provide protection against active influenza virus even with intratumoral administration in our model (FIGS. 5C and 5D), demonstrating a disconnect between anti-tumor and anti-pathogen responses. Since the unique characteristic of AdjFluVx is its squalene-based adjuvant (35, 36), we sought to determine whether this adjuvant is responsible for AdjFluVx's lack of anti-tumor efficacy. Although intratumoral injection of squalene-based adjuvant, AddaVax™ (Adj) (37-39), alone did not alter tumor growth, the addition of Adj to FluVx abrogated FluVx's ability to reduce tumor growth (FIGS. 5E and 5F). Consistent with these tumor growth alterations, analysis of the full NanoString PanCancer Immune Profiling Panel demonstrated a decreased immune signaling signature with AdjFluVx (and with Adj added to FluVx [FluVx+Adj]) compared to FluVx (FIG. 5G). Further, removing the adjuvant from AdjFluVx afforded it the ability to reduce tumor growth (FIGS. 5H and 5I). Although AdjFluVx increased the proportion of DCs among APCs in the tumor (albeit less than FluVx), AdjFluVx did not augment CD8$^+$ T cells (including tumor antigen-specific T cells) within the tumor, ultimately failing to produce the elevated T cell:B cell ratio achieved by FluVx, and instead resulting in elevated influenza virus-specific antibodies in the tumor (FIG. 6A-6E, FIG. 18, FIG. 19). Further, we observed an increased proportion of intra-tumoral regulatory B cells (Bregs; IL-10-producing B cells) with AdjFluVx compared to FluVx administration, without an increase in T regulatory cells (Tregs) (FIGS. 6F and 6G, FIG. 20). Regulatory B cells have been associated with diminished anti-tumor immunity, and IL-10 produced by regulatory B cells can suppress CD8$^+$ T cell functions, thereby abrogating their ability to mount a cytotoxic anti-tumor immune response (9, 40, 41). Importantly, intratu-moral depletion of either B cells or IL-10 rendered AdjFluVx the ability to reduce tumor growth (FIG. 6H-6K).

Discussion

Clinical successes utilizing immunotherapy to improve and prolong the lives of patients with cancer have demon-strated a vital role for the immune system in the treatment for cancer. However, thus far immunotherapies have been able to produce durable responses only in a limited propor-tion of patients. Therefore, to make the next great leap forward, innovative means of engaging the immune system are needed. In our described studies, we have focused on utilizing pathogens to augment inherently weaker anti-tumor immune responses to generate improved local and systemic cancer outcomes. Importantly, we observed that active influ-enza virus injection in the lung reduces tumor growth in the lung (even when a melanoma cell line was used that does not undergo productive infection by active influenza virus). However, active influenza virus injection in the skin did not reduce growth of that same melanoma cell line present in the skin. A difference between the lung and the skin is that the lung inherently contains natural cell targets for active influ-enza virus infection, while the skin does not. Active influ-enza A viruses bind to specific sialic acid residues on epithelial cells in the upper respiratory tract and subsequently gain entry into the cell and replicate, while cells in the skin lack the specific sialic acid residues necessary for productive influenza virus infection (42). Thus, in lung tissue, productive infection leads to a potent immune response to influenza virus by creating an immunologically inflamed "hot" microenvironment in the same tissue as the tumor. Without a major natural target for active influenza virus in the skin, the cells most likely to be affected are dendritic cells, which rather than boosting an immune response are dysregulated when active influenza virus is injected in the skin (28), further decreasing the ability of the tumor microenvironment to become immunologically "hot."

In recent years, viral infection has been harnessed as a vehicle to augment anti-tumor immune responses, and in particular, oncolytic virus (OV) therapy has been employed as a tool in the clinic. Oncolytic viruses preferentially lyse tumor cells and consequently release tumor antigens and danger-associated molecular patterns (DAMPs) (43). How-ever, in the context of oncolytic viruses, productive infection of the tumor cells themselves is the focus. In this setting, the overexpression of specific proteins by tumor cells (but not normal adjacent cells) is hijacked by oncolytic viruses, which use these overexpressed proteins as entry receptors or to facilitate their own replication. Normal cells with less expression of these proteins do not serve as the major target and are spared, or they utilize interferon signaling (a path-way that is dysregulated in cancer cells) to limit infection. Thus, a major focus in this field has centered on the importance of direct infection of the tumor cell as a prereq-uisite for generating anti-tumor immunity. However, the idea that tumor cell lysis by the pathogen is essential has been recently challenged by evidence demonstrating that an inactivated oncolytic virus is capable of initiating anti-tumor immunity via the STING pathway and may support better immunity than its active oncolytic virus counterpart (44). Additionally, our data indicate that TLR activation via interaction with viral-derived PAMPs is increased in the context of inactivated virus, which may initiate an innate immune response and thereby remodel the tumor microen-vironment. Further in support of this is previous research demonstrating that pathogen vaccines can substitute for synthetic TLR agonists to stimulate dendritic cells (45). Our data demonstrate that inactivation of a non-oncolytic virus, such as influenza, can augment an anti-tumor immune response when administered via intratumoral injection, even when the corresponding virus (in active form) is incapable of such activity (as in our setting of active influenza virus administration within a skin melanoma). This indicates that the field of microbial-based cancer therapies (MBCTs), which has experienced a recent resurgence of interest (46, 47), is not limited to the oncolytic class of pathogens or even to the use of active pathogens. Furthermore, in terms of clinical translation, inactivated influenza virus injection can be made available to immunosuppressed patients who are not eligible for active pathogen-based therapies and to patients concerned about sequalae that may result from active pathogen administration.

Studies have reported that pathogen-specific (e.g., CMV, influenza virus, EBV, etc.) CD8$^+$ T cells infiltrate mouse and human tumors and comprise a significant fraction of intra-tumoral CD8$^+$ T cells (48-52). The impact of such anti-viral immune responders on anti-tumor immunity demands fur-ther investigation and may have important implications for the use of MBCTs in the clinic. Interestingly, patients whose tumors harbor the tetrapeptide, ESSA, a sequence shared by CMV, have been shown to exhibit increased survival in the context of CTLA-4 blockade (53). Further, recently in mouse models, virus-specific memory T cells have shown to halt tumor growth when their cognate antigens are injected within the tumor to create an immune-"alarming" effect (49). In contrast to this strategy, which requires previous immunity against a specific pathogen, our work suggests that pathogen-related therapies can be harnessed for anti-tumor immune responses independent of previous exposure, as in the majority of our studies, the hosts had no previous exposure to influenza virus. However, even in such cases, intratumoral administration of inactivated influenza virus increases dendritic cells and anti-tumor CD8$^+$ T cells and consequently the reduction of tumor growth, without any prerequisite immunity. This may be particularly important for repurposing the seasonal "flu shot" for cancer immunotherapy and translating it to clinical care, as the seasonal influenza vaccine includes antigens that are altered yearly to match the anticipated predominant strains of the upcoming season. In this context, our lack of the need for previous exposure to the same pathogen and strain is a major advantage. However, it is also important to note that in our studies, previous infection followed by resolution of a particular strain of influenza virus did not prohibit subsequent tumor reduction with intratumoral inactivated influenza virus (i.e., a vaccine) made from the exact same strain. This suggests that patients with or without previous immunity to the influenza virus strain contained within the utilized "flu shot" may benefit from intratumoral administration of the vaccine. With multiple strains included within each trivalent and quadrivalent "flu shot," it may be that an optimal response is achieved when a combination of new and previously experienced antigens is utilized. In this scenario, previously experienced antigens quickly raise inflammatory immune responses, which inherently are likewise quickly quenched with the elimination of the recognized antigen. At the same time, new antigens raise slower responses that are maintained longer and may have sustained positive effects on anti-tumor immunity.

Our study proposes that intratumoral injection of an unadjuvanted seasonal influenza vaccine reduces tumor growth by converting immunologically inactive "cold" tumors to immune-infiltrated "hot" tumors, by augmenting DCs (including cross-presenting DCs) and tumor antigen-specific CD8$^+$ T cells within the tumor microenvironment. These findings have important implications for the role of intratumoral seasonal influenza vaccination in priming patients to respond to existing immunotherapies (including, PD-1 and CTLA-4 blocking antibodies). Specifically, our study shows that intratumoral seasonal influenza vaccination 1) can reduce tumors on its own, 2) improves outcomes in the context of tumors that respond to PD-L1 therapy, 3) can reduce tumors even when they are resistant to PD-L1 blockade, and 4) in combination with PD-L1 blockade results in drastic reductions in tumor growth. This suggests that in patients, such vaccination may confer increased efficacy of immune-related therapies, including checkpoint blockade treatments that have dramatically improved survival for a segment of the cancer patient population, but which have not yet been made effective for all patients with cancer (54).

Important attention must be paid to the formulation of the vaccine, as some adjuvants may provide improved anti-pathogen protection, while limiting the ability of the vaccine to improve anti-tumor outcomes. The adjuvanted seasonal influenza vaccine utilized in our studies has been demonstrated to provide enhanced immunity against active influenza lung infection in persons 65 years of age and older, whose immunity may decrease with increasing age (33, 34).

However, this adjuvanted formulation does not augment an anti-tumor immune response when administered via intra-tumoral injection, but instead maintains immunosuppressive regulatory B cells within the tumor. Adjuvants play an important role in boosting immune responses. Likely within our unadjuvanted seasonal influenza vaccines natural "adjuvants" (e.g., host cell proteins and DNA, residual influenza ssRNA, etc.) resulting from the process of manufacturing the inactivated seasonal influenza vaccine likewise improve immunity by interacting with multiple danger-sensing mechanisms (e.g. an RNA-sensing toll-like receptor), an interaction that has been previously shown to improve anti-tumor immune responses (55). Since the majority of seasonal influenza vaccines currently on the market are inactivated and do not contain manufactured adjuvants (e.g., squalene), and such vaccines have a high safety profile and are FDA-approved, the translatability of these as innovative immunotherapies for cancer is high and the barriers to reaching many patients with cancer is low.

Although active influenza virus lung infection is a major public health concern, with tens of thousands of deaths documented annually in the United States (56), the Centers for Disease Control and Prevention (CDC) has reported that in the 2017-18 season, only 37.1% of adults received the seasonal influenza vaccine (57). Anecdotally, this percent may be even lower among patients with cancer, in whom infections have also been reported to have greater morbidity and mortality. Importantly, beyond demonstrating that influenza vaccination administered via intratumoral injection can reduce tumor growth, our studies provide evidence that protection against future active influenza lung infection can be provided via intratumoral administration. This suggests that patients receiving intratumoral seasonal influenza vaccination may experience multiple clinical benefits and that seasonal influenza vaccination is a crucial public health tool that may be utilized as both a preventive measure against infection and an immunotherapy for cancer.

Methods

Mice

Mice were housed in specific-pathogen-free (SPF) facilities and all experiments were conducted in accordance with procedures approved by the Institutional Animal Care and Use Committee (IACUC) and Institutional Biosafety Committee (IBC) at Rutgers, The State University of New Jersey and Rush University Medical Center, and the Institutional Review Board (IRB) at Rutgers, The State University of New Jersey. B6 (C57BL/6J), Batf3$^{-/-}$ (B6.129S(C)-Batf3$^{tm1Kmm}$/J), NSG (NOD.Cg-Prkdc$^{scid}$Il2rg$^{tm1wJL}$/SzJ; NOD scid gamma), and Balb/c mice were purchased from Jackson Laboratory at 6-10 weeks of age.

Active Influenza and Heat-Inactivated Influenza Virus

For experiments utilizing active influenza virus infections, mice were administered 1×10$^6$ plaque-forming units (pfu) of A/PR8/1934/H1N1 (FLU) (58) or OVA$_{257-264}$ SIINFEKL-expressing A/PR8/1934/H1 N1 (FLU-OVA) (SEQ ID NO: 1) (59) by passive intranasal (i.n.) or intratumoral (i.e., at the tumor site, i.t.) administration (25-50 μL). Control mice were administered an equal volume of phosphate-buffered saline (PBS) via the same route. For experiments utilizing heat-inactivated influenza virus (hiFLU or hiFLU-OVA), the virus was inactivated by incubating active A/PR8/1934/H1N1 FLU at 90° C. for 5 minutes on an IncuBlock™ Plus heat block (Denville Scientific) prior to injection into mice. For experiments utilizing influenza virus lysate (FLU lysate), active A/PR8/1934/H1N1 FLU was resuspended in RLT buffer (Qiagen) for one hour to generate a lysate. RLT buffer was then dialyzed using a Slide-A-Lyzer™ G2 Dialysis Cassette (10 kDa molecular weight cut-off; ThermoFisher) prior to lysate administration.

Vaccines and Adjuvants

FDA-approved 2017-2018 seasonal influenza vaccines were purchased from their respective manufacturers: FLU-CELVAX® [FluVx1] (Seqirus), FLUVIRIN® [FluVx2] (Seqirus), FLUARIX QUADRIVALENT [FluVx3] (GlaxoSmithKline), FLUBLOK® [FluVx4] (Protein Sciences Corporation), and FLUAD® [AdjFluVx] (Seqirus). Influenza vaccine details are provided in Table 1. Other FDA-approved vaccines were likewise purchased from their respective manufacturers: Infanrix® [DTaP] (GlaxoSmithKline), Pneumovax®23 [Pneumovax; Pneumo] (Merck), EngerixB® [HepB] (GlaxoSmithKline), MMR® [MMR] (Merck). To mimic adjuvant MF59® (Novartis), AddaVax™ [Adj] (Invivogen) was administered via intratumoral injection (50 µL). Control mice were administered PBS at the same volume via the same route. In experiments in which the adjuvant and vaccine were jointly delivered, 50 µL adjuvant+50 µL vaccine were mixed and delivered in a total volume of 100 µL via intratumoral injection. In some experiments, MF59®, which is primarily composed of squalene, was removed by centrifugal filtration using Amicon Ultra Centrifugal Filter Units with regenerated cellulose filters (with a 30 kDa molecular weight cut-off). MF59®- containing AdjFluVx (500 µL) was added to the unit and washed with acetone (250 µL; three times) followed by PBS (250 µL; three times). The protein component of the vaccine was collected using a pipette, freeze dried, and reconstituted to the original volume using PBS.

24 cells via intradermal injection. Cancer cell lines were cultured in DMEM (Gibco), 10% fetal bovine serum (Sigma Aldrich), 100 units/mL penicillin (Gibco), 100 mg/mL streptomycin (Gibco), and 0.29 mg/mL glutamine (Gibco) prior to harvesting for tumor injection. Primary tumor growth was monitored by Vernier caliper measurements in two perpendicular directions serially after tumor challenge. Mice harboring tumors were euthanized when the tumor area reached 20 mm in any direction or met other health-related endpoints, as per institutional IACUC policies. To quantify 4T1 lung metastases, 5% India ink (Fisher Scientific) diluted in distilled water was injected into the trachea after euthanasia. Lungs were dissected and transferred to Fekete's solution [40 mL glacial acetic acid, 32 mL (37%) formalin, 700 mL 100% ethanol, and 228 mL double-distilled water] and washed 3-4 times in this solution and once in PBS. 4T1 lung surface metastases (white in appearance) and B16-F10 lung surface foci (black in appearance) were manually counted with the use of a magnifying glass.

Statistical Analyses

Two-tailed student t test (for two groups) or one-way ANOVA with Tukey correction (for more than two groups) was used to determine statistical significance for data comparisons at a single timepoint. Two-way ANOVA or mixed-effects model with Bonferroni (for two groups) or Tukey (for more than two groups) correction was used to determine statistical significance for data comparisons with multiple timepoints. Kruskal-Wallis with Dunn's Multiple Comparisons test was performed for focused comparisons of one group to all other groups at a single timepoint. Mantel-Cox

TABLE 1

FDA-approved 2017-2018 seasonal unadjuvanted and "adjuvanted" influenza vaccines utilized in the study.

| Influenza vaccine[a] | Manufacturer | Strains | HA/50 µL dose | Adjuvant | Production vehicle | Method of virus inactivation | Solvent |
|---|---|---|---|---|---|---|---|
| FLUCELVAX ® (FluVx1) | Seqirus | Quadrivalent | 6 µg (1.5 µg per strain) | No | MDCK cells | β-propiolactone and cetyltriammonium bromide | Phosphate-buffered saline |
| FLUVIRIN ® (FluVx2) | Seqirus | Trivalent | 4.5 µg (1.5 µg per strain) | No | Embryonated chicken eggs | β-propiolactone | Phosphate-buffered saline |
| FLUARIX ® (FluVx3) | GlaxoSmithKline | Quadrivalent | 6 µg (1.5 µg per strain) | No | Embryonated chicken eggs | Sodium deoxycholate and formaldehyde | Sodium chloride/sodium phosphate |
| FLUBLOK ® (FluVx4) | Protein Sciences Corporation | Quadrivalent | 18 µg (4.5 µg per strain) | No | Sf9 cells | Live virus never infects cells; antigens extracted using Triton-X 100 | Sodium chloride/sodium phosphate |
| FLUAD ® (AdjFluVx) | Seqirus | Trivalent | 4.5 µg (1.5 µg per strain) | Yes (MF59 ®) | Embryonated chicken eggs | Formaldehyde and cetyltriammonium bromide | Oil-water emulsion (MF59 ®) |

[a]Details regarding vaccine manufacturer, the number of influenza virus strains contained within each vaccine, concentration of hemagglutinin (HA) within each 50 µL dose, adjuvant included in the vaccine, vehicle type utilized for vaccine production, method of virus inactivation, and the vaccine solvent utilized, are provided. More information on can be obtained from each vaccine's FDA package insert, which contains full information regarding vaccine formulation and clinical data, and information regarding adjuvants in influenza vaccines can be found at: https://www.cdc.gov/vaccinesafety/concerns/adjuvants.html.

Tumor Challenge

For tumor challenge experiments, B6 and NSG mice were anesthetized with isoflurane and administered 100,000-150,000 B16-F10 melanoma cells (ATCC) via intravenous or intradermal injection and BALB/c mice were anesthetized with isoflurane, administered 100,000-150,000 4T1 triple-negative breast cancer cells (ATCC) in the mammary fat pad or administered 100,000-150,000 CT26 colon carcinoma log rank test was performed to determine statistical significance for the comparison of survival curves. Prism version 8.0 (GraphPad) was used for generation of all graphs and performance of statistical and ESD analyses, except for FIGS. 1C and D, where STATA version 15.0 (StataCorp, LLC) was used to perform statistical analyses. Statistical significance shown for survival curves represents a comparison of the two survival curves. Statistical significance shown for all other graphs represents comparisons at the indicated timepoint. Statistical significance is denoted as ns, not significant, *P<0.05, P<0.01, and *P<0.001. Comparisons with significance at P<0.001 or P<0.0001 are listed as ***P<0.001.

SEER-Medicare Linked Database Subjects

Study subjects were identified from the SEER-Medicare Linked Database and SAS version 9.4 (SAS Institute, Inc.) was used to analyze these data. All cases of primary stage I to II non-small cell lung cancer (NSCLC; tumor site codes 34.0-34.9 and ICD-O-2 morphology codes 8010-8040, 8050-8076, 8140, 8143, 8250-8260, 8310, 8320, 8323, 8470-8490, and 8550-8573), age >65 years, treated with either surgery or chemo-radiation during the span of a 100 months between 2001 and 2011 were included. Samples were limited to patients with histologically confirmed cancers and excluded cases diagnosed at autopsy or death certificate. Survival was determined as the interval from the date of cancer diagnosis to the Medicare date of death. These data are updated daily by Medicare and thus are current as of the day that data were extracted for linkage with SEER. For analyses involving lung-cancer specific survival, SEER survival data were used as Medicare does not provide information regarding the cause of death. Data on the cause of death in SEER were obtained from state death certificates and included in the PEDSF file using ICD-9 codes. Presence of influenza virus infection was considered 'yes' (FLU dx) based on codes obtained from MEDPAR files for hospitalization for influenza virus infection. Since lung cancer-specific mortality did not reach 50% for the FLU dx group, time to mortality (lung cancer-specific and overall) in 25% of the patients (P25) was calculated.

Autologous Immune-Reconstituted Patient-Derived Xenograft (AIR-PDX) Mouse Model

Immune-deficient NSG mice were purchased from Jackson Laboratory and bred in-house. Patient-derived tumor tissue and peripheral blood were obtained with patient consent and under IRB approval through the Rutgers Cancer Institute of New Jersey Biospecimen Repository and Histopathology Service, which serves as an "honest broker" and maintains the chain of custody for patient samples made available to investigators at Rutgers Cancer Institute of New Jersey. Two sets of AIR-PDX mice were created, one set from a patient whose de-identified clinical annotation described the tissue as a primary lung tumor and one from a patient whose clinical annotation defined the tissue as a melanoma metastasis to lymph node. AIR-PDX mice were created within 24 hours of obtaining autologous (i.e., from the same patient) tumor tissue and peripheral blood. Specifically, male and female NSG mice (>8 weeks of age) received adoptive transfer (via intraperitoneal injection [i.p]) of fresh peripheral blood mononuclear cells (PBMCs) after extraction from peripheral blood by Ficoll gradient centrifugation. PBMCs were washed and re-suspended in PBS for injection (500,000 cells in 100 μL per mouse). Additionally, these NSG mice were surgically implanted with fresh tumor (~5×5×3 mm tumor sections; one per mouse) into a 5-mm incision made in the right flank and closed with a 6-0 proline horizontal mattress suture (Henry Schein). Mice recovered from this minor survival surgery in warming cages and were monitored for assurance of a minimum respiratory rate of 30 breaths/minute. Within two weeks of adoptive transfer and surgery, AIR-PDX mice were surveyed for successful tumor implantation (defined as stable or increasing tumor size compared to implantation size). Subsequently, AIR-PDX mice created from a patient-derived primary lung tumor received intratumoral FluVx (FluVx1) or PBS on day 0 (i.e., the first day of treatment), and AIR-PDX created from a patient-derived melanoma lymph node metastasis received intratumoral FluVx (FluVx1) or PBS on days 0 and 2.

Depletions, Blockade, and Adoptive Cell Transfer

In vivo antibody-mediated depletions and blockades were performed using the following antibodies: aCD20 (BioLegend, clone SA271G2), αCD8 (BioXCell, clone 2.43), αIL-10 (BioXCell, clone JES5-2A5), and aPD-L1 (BioXCell, clone 10F.9G2), or their respective isotype control antibodies. Antibodies were diluted to desired concentrations in InVivoPure pH 6.5 Dilution Buffer (BioXCell) and administered at either 250 μg via intraperitoneal injection or 50 μg via intratumoral injection. In experiments requiring transfer of splenic cells from donor to recipient mice, spleens were mechanically dissociated through a 70-μm filter and red blood cells were removed using 1 mL of Ack Lysing Buffer (Gibco) per spleen under sterile conditions. Cells were washed and re-suspended in PBS and adoptively transferred to recipient mice (~5×10$^7$) via intraperitoneal (i.p.) injection in a total volume of 100 μL.

Tissue Processing and Flow Cytometry

For optimal staining of IL-10, 500 μg of monensin (Sigma-Aldrich) dissolved in dimethyl sulfoxide (DMSO) (Sigma Aldrich) was administered via i.v. injection (retro-orbital sinus) into mice six hours prior to euthanasia and dissection. Resected tumors were mechanically dissociated using a gentleMACS™ Octo Dissociator utilizing program Tumor 01_01 (Miltenyi Biotec) in HBSS, enzymatically dissociated in HBSS containing 1 mg/mL type IV collagenase from Clostridium histolyticum (Sigma-Aldrich) and 40 μgmL DNAse I from bovine pancreas (Sigma-Aldrich) at 37° C. for 30 minutes with constant rocking, and then mechanically dissociated using Dissociator program Tumor 02_01. Dissociated cells were applied to a 70-μm filter and subsequently washed with PBS to yield a single-cell suspension. Spleens were mechanically dissociated through a 70-μm filter and red blood cells were removed using 1 mL of Ack Lysing Buffer per spleen. Cells were washed with PBS prior to staining for flow cytometry. H-2Db gp100 dextramer, KVPRNQDWL (SEQ ID NO: 2) (Immudex), and H-2Kb TRP2 dextramer, SVYDFFVWL (SEQ ID NO: 3) (Immudex), were applied to cells at a concentration of 5 μL/dextramer in a total volume of 50 μL PBS for 20 minutes at room temperature. Extracellular staining was subsequently performed using antibodies specific to CD3, CD4, CD8, CD11c, CD19, CD20, CD45, H-2Kb-SIINFEKL (OVA$_{257-264}$) (SEQ ID NO: 1), and MHC-II, purchased from either BioLegend or eBiosciences/ThermoFisher Scientific, using 1-5 μL/test in a total volume of 100 μL PBS for 30 minutes at room temperature. The LIVE/DEAD Fixable Aqua Dead Cell Stain Kit for 450 nm excitation (ThermoFisher Scientific) at 0.25 μL/test was added to each sample. Cells were washed with PBS before proceeding to intracellular staining steps. Intracellular staining was performed using the True-Nuclear™ Transcription Buffer Set (BioLegend), in accordance with manufacturer's protocol. Antibodies selective for FOXP3 and IL-10 (eBiosciences/ThermoFisher Scientific) were used at 1-5 μL/test in a total of 100 μL of 1× Perm Buffer (BioLegend). Cells were washed three times in Perm Buffer and fixed using BD™ Stabilizing Fixative (Becton Dickinson). Flow cytometry was performed using a BD LSR II cytometer. Analysis of flow cytometry was performed using Flow Jo (TreeStar, version 10). Flow plots shown have undergone gating on live singlet lymphocytes utilizing forward scatter (FSC) and side scatter (SSC) height, area, and width, as well as LIVE/DEAD, as previously described (60).

Quantitative PCR and NanoString Analysis

Dissected tumors and lungs were stored in 1 mL of TRIzol™ (Invitrogen) at −80° C. until RNA extraction was performed. Subsequently, tissues were homogenized using Benchmark's BEADBUG™ 6 Microtube Homogenizer. RNA was isolated using the Qiagen RNeasy Plus Mini Kit. The purity of the resulting RNA was measured using a NanoDrop™ spectrophotometer (Thermo Fisher Scientific). Quantitative reverse transcription polymerase chain reaction (qRT-PCR) for influenza virus was performed using the primers 5' CATGGAATGGCTAAAGACAAGACC (SEQ ID NO: 4) (forward), 5' CCATTAAGGGCATTTTGGACA (SEQ ID NO: 5) (reverse), and the TaqMan® probe FAM-5' TTTGTGTTCACGCTCACCGTGCCCA TAMRA-3' (SEQ ID NO: 6) (ThermoFisher Scientific). GAPDH was used as a housekeeping gene control. qRT-PCR was conducted using a StepOnePlus Real-Time PCR System (Applied Biosystems). Profiling of transcripts implicated in the anti-tumor immune response was assessed via the NanoString PanCancer Immune Profiling Panel using an nCounter Digital Analyzer (NanoString Technologies). Total RNA (100 ng) was used for each sample analyzed. Analysis of NanoString data was performed using nSolver Analysis software.

T Cell Receptor (TCR) Sequencing and Analysis

Tumors were frozen at −80° C. upon dissection. Samples were analyzed by Adaptive Biotechnologies utilizing the immunoSEQ® assay, which assesses diversity and clonality of the CDR3 region of the TCR of T cells. Sequences were characterized by utilizing a multiplex PCR strategy followed by Illumine sequencing (2-6). Data were analyzed using immunoSEQ® Analyzer software and Excel (Microsoft). To determine whether TCR clones within the tumor microenvironment of a control (PBS-injected) tumor are expanded with FluVx treatment (i.e., demonstrate increased clonality/evenness), the mean representation of tumor-associated TCR clones was analyzed. Productive TCR clones were derived from FluVx1-treated and control tumors and compared. TCR clones from control tumors were considered "tumor-associated." Tumor-associated TCR clones represented in at least one control tumor (n) and detected in a greater number of FluVx1-treated tumors (at least n+1) were further considered. Among these TCR clones, average clonality within control tumors was compared to FluVx1-treated tumors and a graph was generated.

Influenza Virus Antibody ELISA

Nunc MaxiSorp flat-bottom plates (ThermoFisher Scientific) were coated with either FluVx1 or AdjFluVx at a concentration of 1 µgmL diluted in PBST to a total volume per well of 100 µL. As a negative control, select wells were incubated with 100 µL of PBS without vaccine. After overnight incubation, the coating solution was discarded, and wells were washed once with 100 µL PBST buffer (PBS buffer with 0.05% Tween20). Plates were then blocked with 5% milk powder in PBST at 100 µL/well for one hour. Wells were subsequently washed three times with 100 µL PBST. Then, tumor homogenates were added to the wells at 1:1000 dilution with PBST at a final volume of 100 µL and incubated for one hour. Plates were subsequently washed five times in 100 µL PBST and then 100 µL TMB substrate was added to each well for three minutes. Next, 50 µL of stop solution ($H_2SO_4$) was added to each well. Contents of each well were transferred to a new plate and absorbance was read at 450 nm. Absorbance for each experimental well was calculated by subtracting background absorbance (derived from coated control wells in which PBST was added in place of tumor homogenate).

Toll-Like Receptor (TLR) Signaling Assay

The HEK-Blue-mTLR7 cell line (Invivogen), engineered to express mouse TLR7 (mTLR7), and its parental cell line, Null2-k (Invivogen), which does not express any mouse TLRs, were propagated and utilized to determine TLR7 activity, as per the manufacturer's instructions. In HEK-Blue-mTLR7 cells, secreted embryonic alkaline phosphatase (SEAP) is produced upon stimulation with a TLR7 ligand and real-time detection of SEAP is conducted utilizing HEK-Blue Detection medium (Invivogen) (7). Briefly, treatments and controls were plated in triplicate: 20 µl of active (MOI=1) or heat-inactivated influenza A/PR8/1934/H1N1 virus, positive control TLR7 agonist, CL264 (50 µg/ml, Invivogen), and negative control, PBS (1×). Then, the respective cell lines ($5 \times 10^4$ cells in 180 µl of medium per well) were added to the appropriate wells. The plate was incubated for 24 hours at 37° C. and 5% CO2, and analyzed using a Cytation 3 (Biotek) plate reader at $OD_{620\ nm}$.

Unless otherwise defined, scientific and technical terms used in connection with this disclosure shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout this disclosure. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. Generally, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference. As utilized in accordance with this disclosure, the terms defined in this disclosure, unless otherwise indicated, shall be understood to have the meanings as defined herein.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1. M. Binnewies et al., Understanding the tumor immune microenvironment (TIME) for effective therapy. *Nature medicine* 24, 541-550 (2018).
2. R. Cristescu et al., Pan-tumor genomic biomarkers for PD-1 checkpoint blockade-based immunotherapy. *Science* 362 (2018).
3. T. F. Gajewski et al., Cancer Immunotherapy Targets Based on Understanding the T Cell-Inflamed Versus Non-T Cell-Inflamed Tumor Microenvironment. *Advances in experimental medicine and biology* 1036, 19-31 (2017).
4. J. Galon, D. Bruni, Approaches to treat immune hot, altered and cold tumours with combination immunotherapies. Nature reviews. *Drug discovery* 10.1038/541573-018-0007-y (2019).
5. M. Ayers et al., IFN-gamma-related mRNA profile predicts clinical response to PD-1 blockade. *The Journal of clinical investigation* 127, 2930-2940 (2017).
6. L. Martinez-Lostao, A. Anel, J. Pardo, How Do Cytotoxic Lymphocytes Kill Cancer Cells? *Clinical Cancer Research* 21, 5047-5056 (2015).
7. J. N. Kather et al., Topography of cancer-associated immune cells in human solid tumors. *eLife* 7 (2018).
8. D. Lindau, P. Gielen, M. Kroesen, P. Wesseling, G. J. Adema, The immunosuppressive tumour network: myeloid-derived suppressor cells, regulatory T cells and natural killer T cells. *Immunology* 138, 105-115 (2013).
9. C. Mauri, M. Menon, Human regulatory B cells in health and disease: therapeutic potential. *The Journal of clinical investigation* 127, 772-779 (2017).
10. A. H. Sharpe, Introduction to checkpoint inhibitors and cancer immunotherapy. *Immunological reviews* 276, 5-8 (2017).
11. X. Bu, K. M. Mahoney, G. J. Freeman, Learning from PD-1 Resistance: New Combination Strategies. *Trends in molecular medicine* 22, 448-451 (2016).
12. S. L. Topalian et al., Five-Year Survival and Correlates Among Patients With Advanced Melanoma, Renal Cell Carcinoma, or Non-Small Cell Lung Cancer Treated With Nivolumab. *JAMA oncology* 10.1001/jamaoncol.2019.2187 (2019).
13. R. W. Wilkinson, A. J. Leishman, Further Advances in Cancer Immunotherapy: Going Beyond Checkpoint Blockade. *Frontiers in immunology* 9, 1082-1082 (2018).
14. M. Y. Mapara, M. Sykes, Tolerance and Cancer: Mechanisms of Tumor Evasion and Strategies for Breaking Tolerance. *Journal of Clinical Oncology* 22, 1136-1151 (2004).
15. A. Makkouk, G. J. Weiner, Cancer immunotherapy and breaking immune tolerance: new approaches to an old challenge. *Cancer research* 75, 5-10 (2015).
16. H. Uchi et al., Unraveling the complex relationship between cancer immunity and autoimmunity: lessons from melanoma and vitiligo. *Advances in immunology* 90, 215-241 (2006).
17. E. D. Thompson, H. L. Enriquez, Y. X. Fu, V. H. Engelhard, Tumor masses support naive T cell infiltration, activation, and differentiation into effectors. *J Exp Med* 207, 1791-1804 (2010).
18. J. H. Newman, A. Zloza, Infection: a Cause of and Cure for Cancer. *Current pharmacology reports* 3, 315-320 (2017).
19. U. K. lheagwara et al., Influenza virus infection elicits protective antibodies and T cells specific for host cell antigens also expressed as tumor-associated antigens: a new view of cancer immunosurveillance. *Cancer immunology research* 2, 263-273 (2014).
20. M. Kohler, B. Ruttner, S. Cooper, H. Hengartner, R. M. Zinkernagel, Enhanced tumor susceptibility of immuno-competent mice infected with lymphocytic choriomeningitis virus. *Cancer immunology, immunotherapy: CI32*, 117-124 (1990).
21. S. A. Hoption Cann, J. P. van Netten, C. van Netten, Acute infections as a means of cancer prevention: opposing effects to chronic infections? *Cancer detection and prevention* 30, 83-93 (2006).
22. F. J. Kohlhapp et al., Non-oncogenic Acute Viral Infections Disrupt Anti-cancer Responses and Lead to Accelerated Cancer-Specific Host Death. *Cell reports* 17, 957-965 (2016).
23. L. J. Old, D. A. Clarke, B. Benacerraf, Effect of Bacillus Calmette-Guerin infection on transplanted tumours in the mouse. *Nature* 184(Suppl 5), 291-292 (1959).
24. L. H. Dang, C. Bettegowda, D. L. Huso, K. W. Kinzler, B. Vogelstein, Combination bacteriolytic therapy for the treatment of experimental tumors. *Proceedings of the National Academy of Sciences* 98, 15155-15160 (2001).
25. G. Xin et al., Pathogen boosted adoptive cell transfer immunotherapy to treat solid tumors. *Proceedings of the National Academy of Sciences* 114, 740-745 (2017).
26. S. A. Rosenberg, P. J. Spiess, D. E. Kleiner, Antitumor effects in mice of the intravenous injection of attenuated Salmonella typhimurium. *Journal of immunotherapy* 25, 218-225 (2002).
27. W. B. Coley, The Treatment of Inoperable Sarcoma by Bacterial Toxins (the Mixed Toxins of the *Streptococcus erysipelas* and the *Bacillus prodigiosus*). *Proceedings of the Royal Society of Medicine* 3, 1-48 (1910).
28. A. Smed-Sorensen et al., Influenza A virus infection of human primary dendritic cells impairs their ability to cross-present antigen to CD8 T cells. *PLoS pathogens* 8, e1002572 (2012).
29. K. Hildner et al., Batf3 deficiency reveals a critical role for CD8alpha+ dendritic cells in cytotoxic T cell immunity. *Science* 322, 1097-1100 (2008).
30. L. Hammerich et al., Systemic clinical tumor regressions and potentiation of PD1 blockade with in situ vaccination. *Nature medicine* 25, 814-824 (2019).
31. L. D. Shultz et al., Human lymphoid and myeloid cell development in NOD/LtSz-scid IL2R gamma null mice engrafted with mobilized human hemopoietic stem cells. *Journal of immunology* 174, 6477-6489 (2005).
32. P. C. Tumeh et al., PD-1 blockade induces responses by inhibiting adaptive immune resistance. *Nature* 515, 568-571 (2014).
33. T. F. Tsai, Fluad(R)-MF59(R)-Adjuvanted Influenza Vaccine in Older Adults. *Infection & chemotherapy* 45, 159-174 (2013).
34. S. Khurana et al., MF59 adjuvant enhances diversity and affinity of antibody-mediated immune response to pandemic influenza vaccines. *Science translational medicine* 3, 85ra48 (2011).
35. D. T. O'Hagan, G. S. Ott, E. De Gregorio, A. Seubert, The mechanism of action of MF59—an innately attractive adjuvant formulation. *Vaccine* 30, 4341-4348 (2012).
36. N. P. Knudsen et al., Different human vaccine adjuvants promote distinct antigen-independent immunological signatures tailored to different pathogens. *Scientific reports* 6, 19570 (2016).
37. M. A. Tegenge et al., Pharmacokinetics and biodistribution of squalene-containing emulsion adjuvant following intramuscular injection of H5N1 influenza vaccine in mice. *Regulatory toxicology and pharmacology: RTP* 81, 113-119 (2016).

38. P. H. Goff et al., Adjuvants and immunization strategies to induce influenza virus hemagglutinin stalk antibodies. *PloS one* 8, e79194 (2013).

39. E. Sasaki et al., Modeling for influenza vaccines and adjuvants profile for safety prediction system using gene expression profiling and statistical tools. *PloS one* 13, e0191896 (2018).

40. G. J. Yuen, E. Demissie, S. Pillai, B lymphocytes and cancer: a love-hate relationship. *Trends in cancer* 2, 747-757 (2016).

41. E. C. Rosser, C. Mauri, Regulatory B cells: origin, phenotype, and function. *Immunity* 42, 607-612 (2015).

42. U. Kumlin, S. Olofsson, K. Dimock, N. Arnberg, Sialic acid tissue distribution and influenza virus tropism. *Influenza and other respiratory viruses* 2, 147-154 (2008).

43. H. L. Kaufman, F. J. Kohlhapp, A. Zloza, Oncolytic viruses: a new class of immunotherapy drugs. *Nature reviews. Drug discovery* 14, 642-662 (2015).

44. P. Dai et al., Intratumoral delivery of inactivated modified vaccinia virus Ankara (iMVA) induces systemic antitumor immunity via STING and Batf3-dependent dendritic cells. *Science immunology* 2 (2017).

45. G. Schreibelt et al., Commonly used prophylactic vaccines as an alternative for synthetically produced TLR ligands to mature monocyte-derived dendritic cells. *Blood* 116, 564-574 (2010).

46. A. Zloza, Viruses, bacteria, and parasites—oh my! a resurgence of interest in microbial-based therapy for cancer. *Journal for immunotherapy of cancer* 6, 3 (2018).

47. N. S. Forbes et al., White paper on microbial anti-cancer therapy and prevention. *Journal for immunotherapy of cancer* 6, 78 (2018).

48. Y. Simoni et al., Bystander CD8(+) T cells are abundant and phenotypically distinct in human tumour infiltrates. *Nature* 557, 575-579 (2018).

49. P. C. Rosato et al., Virus-specific memory T cells populate tumors and can be repurposed for tumor immunotherapy. *Nature communications* 10, 567 (2019).

50. P. Kvistborg et al., TIL therapy broadens the tumor-reactive CD8(+) T cell compartment in melanoma patients. *Oncoimmunology* 1, 409-418 (2012).

51. R. S. Andersen et al., Dissection of T-cell antigen specificity in human melanoma. *Cancer research* 72, 1642-1650 (2012).

52. D. A. Erkes et al., Virus-Specific CD8(+) T Cells Infiltrate Melanoma Lesions and Retain Function Independently of PD-1 Expression. *Journal of immunology* 198, 2979-2988 (2017).

53. A. Snyder et al., Genetic basis for clinical response to CTLA-4 blockade in melanoma. *The New England journal of medicine* 371, 2189-2199 (2014).

54. H. O. Alsaab et al., PD-1 and PD-L1 Checkpoint Signaling Inhibition for Cancer Immunotherapy: Mechanism, Combinations, and Clinical Outcome. *Frontiers in pharmacology* 8, 561-561 (2017).

55. G. Shayan et al., Phase Ib Study of Immune Biomarker Modulation with Neoadjuvant Cetuximab and TLR8 Stimulation in Head and Neck Cancer to Overcome Suppressive Myeloid Signals. *Clinical cancer research: an official journal of the American Association for Cancer Research* 24, 62-72 (2018).

56. Y. Young-Xu, R. van Aalst, E. Russo, J. K. H. Lee, A. Chit, The Annual Burden of Seasonal Influenza in the US Veterans Affairs Population. *PloS one* 12, e0169344-e0169344 (2017).

57. CDC (2018) httPs://www.cdc.gov/flu/flueaxview/coverage-1718estimates.htm.

58. J. A. Rutigliano et al., Highly pathological influenza A virus infection is associated with augmented expression of PD-1 by functionally compromised virus-specific CD8⁺ T cells. *Journal of virology* 88, 1636-1651 (2014).

59. M. R. Jenkins, R. Webby, P. C. Doherty, S. J. Turner, Addition of a prominent epitope affects influenza A virus-specific CD8⁺ T cell immunodominance hierarchies when antigen is limiting. *Journal of immunology* 177, 2917-2925 (2006).

60. A. Zloza et al., NKG2D signaling on CD8(+) T cells represses T-bet and rescues CD4-unhelped CD8(+) T cell memory recall but not effector responses. Nature medicine 18, 422-428 (2012).

61. C. S. Carlson et al., Using synthetic templates to design an unbiased multiplex PCR assay. Nature communications 4, 2680 (2013).

62. H. S. Robins et al., Comprehensive assessment of T-cell receptor beta-chain diversity in alphabeta T cells. Blood 114, 4099-4107 (2009).

63. M. Yousfi Monod, V. Giudicelli, D. Chaume, M. P. Lefranc, IMGT/JunctionAnalysis: the first tool for the analysis of the immunoglobulin and T cell receptor complex V-J and V-D-J JUNCTIONs. Bioinformatics 20 Suppl 1, i379-385 (2004).

64. R. O. Emerson et al., High-throughput sequencing of T-cell receptors reveals a homogeneous repertoire of tumour-infiltrating lymphocytes in ovarian cancer. The Journal of pathology 231, 433-440 (2013).

65. D. Wu et al., High-throughput sequencing detects minimal residual disease in acute T lymphoblastic leukemia. Science translational medicine 4, 134ra163 (2012).

66. M. C. Serradell et al., Efficient oral vaccination by bioengineering virus-like particles with protozoan surface proteins. Nature communications 10, 361 (2019).

The invention claimed is:

1. A method of treating cancer in a subject in need thereof comprising:

intratumorally administering a therapeutically effective dose of an inactivated influenza vaccine to the subject, wherein the cancer is selected from the group consisting of melanoma, lung, triple-negative breast, or renal; and wherein the vaccine is unadjuvanted.

2. The method of claim 1, wherein the vaccine is a monovalent or a multivalent vaccine.

3. The method of claim 1, wherein the inactivated influenza vaccine is administered in combination with an inactive vaccine selected from the group consisting of DTaP (diphtheria, pertussis and tetanus), pneumococcal polysaccharide vaccine (Pneumococcal Pneumonia), HepB (hepatitis B), and MMR (measles, mumps, rubella).

4. The method according to claim 1, wherein multiple doses of the inactivated influenza vaccine are administered.

5. The method according to claim 1, wherein the intratumoral administration is by injection or during a biopsy procedure.

6. The method according to claim 1, further comprising administering at least one additional anticancer treatment.

7. The method of claim 6, wherein the at least one additional anticancer treatment is surgical therapy, chemotherapy, radiation therapy, hormonal therapy, immunotherapy, small molecule therapy, receptor kinase inhibitor therapy, anti-angiogenic therapy, cytokine therapy, cryotherapy, radioablation or a biological therapy.

8. The method of claim 6, wherein the at least one additional anticancer treatment is an immune checkpoint inhibitor.

9. The method of claim 8, wherein the at least one checkpoint inhibitor is selected from an inhibitor of Programmed T cell death 1 (PD-1), programmed T cell death ligand 1 (PD-L1), PDL-2, Cytotoxic T-lymphocyte antigen 4 (CTLA-4), Lymphocyte-activation gene 3 (LAG-3), Tim-3, CD28, CD122, or CD137.

10. The method of claim 9, wherein the at least one checkpoint inhibitor is an anti-PD-1 antibody, anti-PD-L1 antibody, anti-PD-L2 antibody, anti-CTLA4 antibody, or anti-LAG3 antibody.

11. The method of claim 10, wherein the anti-PD-1 antibody is selected from the group consisting of nivolumab, pembrolizumab, pidilizumab, AMP-514, REGN2810, CT-011, BMS 936559, MPDL3280A and AMP-224, wherein the anti-PD-L1 antibody is selected from the group consisting of durvalumab, atezolizumab, and avelumab and wherein the anti-CTLA-4 antibody is tremelimumab or ipilimumab.

12. The method of claim 8, wherein more than one checkpoint inhibitor is administered.

13. A method of increasing an immune response in a tumor in a subject in need thereof, the method comprising:
intratumorally administering a therapeutically effective dose of an inactive influenza vaccine to the subject,
wherein the tumor is a melanoma tumor, a lung tumor, a triple-negative breast cancer tumor, or a kidney tumor.

14. The method of claim 13, wherein the inactive influenza vaccine is a non-intratumoral B-cell promoting vaccine.

15. The method of claim 1, wherein the cancer is melanoma.

16. The method of claim 3, wherein the cancer is melanoma.

17. The method of claim 1, wherein vaccine lacks a squalene-based adjuvant.

18. A method of treating cancer in a subject in need thereof comprising:
intratumorally administering a therapeutically effective dose of an inactivated vaccine to the subject,
wherein the inactivated vaccine is selected from the group consisting of DTaP (diphtheria, pertussis, and tetanus), pneumococcal polysaccharide vaccine (Pneumococcal Pneumonia), HepB (hepatitis B), and MMR (measles, mumps, rubella);
wherein the cancer is selected from the group consisting of melanoma or colon cancer; and
wherein the vaccine is unadjuvanted.

19. The method of claim 18, wherein vaccine lacks a squalene-based adjuvant.

*     *     *     *     *

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: ovalbumin peptide
```

```
<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Artificial Sequence
<220> FEATURE:
<223> OTHER INFORMATION: H-2Db gp100 dextramer

<400> SEQUENCE: 2

Lys Val Pro Arg Asn Gln Asp Trp Leu
1               5

<210> SEQ ID NO 3
<211> LENGTH: 9
<212> TYPE: PRT
<213> ORGANISM: Artificial Sequence
<220> FEATURE:
<223> OTHER INFORMATION: H-2Kb TRP2 dextramer

<400> SEQUENCE: 3

Ser Val Tyr Asp Phe Phe Val Trp Leu
1               5

<210> SEQ ID NO 4
<211> LENGTH: 24
<212> TYPE: DNA
<213> ORGANISM: Artificial Sequence
<220> FEATURE:
<223> OTHER INFORMATION: influenza forward primer

<400> SEQUENCE: 4
catggaatgg ctaaagacaa gacc                                      24

<210> SEQ ID NO 5
<211> LENGTH: 21
<212> TYPE: DNA
<213> ORGANISM: Artificial Sequence
<220> FEATURE:
<223> OTHER INFORMATION: influenza reverse primer

<400> SEQUENCE: 5
ccattaaggg cattttggac a                                         21

<210> SEQ ID NO 6
<211> LENGTH: 25
<212> TYPE: DNA
<213> ORGANISM: Artificial Sequence
<220> FEATURE:
<223> OTHER INFORMATION: Taqman probe

<400> SEQUENCE: 6
tttgtgttca cgctcaccgt gccca                                     25
```